US009594089B2

(12) United States Patent
Ootani et al.

(10) Patent No.: US 9,594,089 B2
(45) Date of Patent: Mar. 14, 2017

(54) ANALYZING APPARATUS, SOLID-LIQUID SEPARATION DEVICE AND SOLID-LIQUID SEPARATION METHOD

(71) Applicant: Sysmex Corporation, Kobe-shi, Hyogo (JP)

(72) Inventors: Toshihiro Ootani, Kobe (JP); Kazuya Fukuda, Kobe (JP); Kazunori Mototsu, Kobe (JP)

(73) Assignee: SYSMEX CORPORATION, Kyogo (JP)

( * ) Notice: Subject to any disclaimer, the term of this patent is extended or adjusted under 35 U.S.C. 154(b) by 0 days.

(21) Appl. No.: 14/662,741

(22) Filed: Mar. 19, 2015

(65) Prior Publication Data
US 2015/0198621 A1 Jul. 16, 2015

Related U.S. Application Data

(63) Continuation of application No. 11/656,802, filed on Jan. 23, 2007, now abandoned.

(30) Foreign Application Priority Data

Jan. 23, 2006 (JP) .................. 2006-013429
Mar. 31, 2006 (JP) .................. 2006-096483

(51) Int. Cl.
G01N 35/04 (2006.01)
B01F 11/00 (2006.01)
G01N 35/00 (2006.01)
G01N 35/02 (2006.01)
G01N 35/10 (2006.01)

(52) U.S. Cl.
CPC ..... *G01N 35/0098* (2013.01); *G01N 35/0099* (2013.01); *G01N 35/025* (2013.01); *G01N 2035/1088* (2013.01)

(58) Field of Classification Search
None
See application file for complete search history.

(56) References Cited

U.S. PATENT DOCUMENTS

| 4,647,432 A | 3/1987 | Wakatake |
| 5,183,638 A | 2/1993 | Wakatake |
| 5,474,744 A * | 12/1995 | Lerch ................. G01N 35/1004 134/169 R |
| 5,587,129 A | 12/1996 | Kurosaki et al. |
| 5,642,938 A | 7/1997 | Nakagawa et al. |
| 5,698,450 A * | 12/1997 | Ringrose ............ G01N 35/0092 422/63 |
| 5,885,529 A | 3/1999 | Babson et al. |

(Continued)

FOREIGN PATENT DOCUMENTS

| JP | 63-289450 | 11/1988 |
| JP | 03-175361 | 7/1991 |

(Continued)

*Primary Examiner* — P. Kathryn Wright
(74) *Attorney, Agent, or Firm* — Brinks Gilson & Lione

(57) ABSTRACT

An analyzing apparatus is described, a representative one of which includes: rotatable table arranged with a plurality of holes for accommodating the reaction container which includes a specimen and a reagent; and a container transferring section, arranged on the rotatable table, for transferring the reaction container.

18 Claims, 17 Drawing Sheets

(56) References Cited

U.S. PATENT DOCUMENTS

| | | | |
|---|---|---|---|
| 5,885,530 A * | 3/1999 | Babson | B01L 3/50853 |
| | | | 422/63 |
| 6,331,277 B2 | 12/2001 | Tajima | |
| 6,537,434 B1 | 3/2003 | McGrath et al. | |
| 7,171,863 B2 | 2/2007 | Tamura et al. | |
| 2002/0137197 A1* | 9/2002 | Ammann | B01F 9/0001 |
| | | | 435/287.2 |
| 2003/0049170 A1 | 3/2003 | Tamura et al. | |
| 2007/0110617 A1* | 5/2007 | Nagai | G01N 35/026 |
| | | | 422/65 |
| 2007/0110627 A1 | 5/2007 | Nagai et al. | |
| 2014/0065018 A1* | 3/2014 | Imazu | G01N 35/04 |
| | | | 422/73 |

FOREIGN PATENT DOCUMENTS

| | | |
|---|---|---|
| JP | 05-040122 | 2/1993 |
| JP | 06-160401 | 6/1994 |
| JP | 08-062224 | 3/1996 |
| JP | 09-089907 | 4/1997 |
| JP | 2001-091521 | 4/2001 |
| JP | 2002-168866 | 6/2002 |
| JP | 2003-083992 | 3/2003 |
| WO | WO88/02866 | 4/1988 |

\* cited by examiner

ANALYZING APPARATUS, SOLID-LIQUID SEPARATION DEVICE AND SOLID-LIQUID SEPARATION METHOD

This application claims priority under 35 U.S.C. §119 to Japanese Patent Application No. JP2006-013429 filed Jan. 23, 2006, Japanese Patent Application No. JP2006-096483 filed Mar. 31, 2006, and U.S. patent application Ser. No. 11/656,802 filed Jan. 23, 2007, the entire content of which is hereby incorporated by reference.

FIELD OF THE INVENTION

The present invention relates to analyzing apparatus, in particular, to an analyzing apparatus including a container transferring section for transferring a reaction container accommodating a reaction sample prepared by reacting a specimen and a reagent, and an analyzing apparatus a solid-liquid separation device and a solid-liquid separation method for using a reagent having magnetic particles as a solid phase.

BACKGROUND OF THE INVENTION

Analyzing devices such as colorimetric analyzing device, fluorometric analyzing device, immune analyzing device and blood coagulation analyzing device are conventionally known as a device for accommodating the reaction sample prepared from the specimen and the reagent in the reaction container, irradiating light from the light source onto the reaction container and analyzing various aspects of the specimen.

In this type of analyzing device, the specimen and the reagent are dispensed in the reaction container. The specimen and the reagent are then stirred and warmed (incubated) over a predetermined time to prepare a reaction sample. The sample preparing steps depend on the measurement items and the measurement principle, and most steps involve adding a plurality of reagents to the specimen.

In one example of preparing the sample by the immune analyzing device, the specimen dispensed in the reaction container and a first reagent containing trapped antibody are first stirred and warmed as described above to prepare a sample in which the antigen contained in the specimen and the trapped antibody are bound. The mixed solution obtained by adding a second reagent containing the magnetic particles to the relevant sample is then stirred and warmed to prepare a sample in which the magnetic particles and the trapped antibody are bound. The magnet is brought close to the reaction sample to separate the bound antigen, trapped antibody and magnetic particles, and the unnecessary components, and the reaction liquid is suctioned and cleaned to remove the unnecessary components from the sample (BF separation).

A third reagent containing labeled antibody that binds with the antigen in the specimen is added to the sample removed with the unnecessary components, and the mixed solution is stirred and warmed to prepare a sample in which the antigen bound with the magnetic particles and the labeled antibody are bound. The BF separation similar to the above is performed on the relevant sample to remove the unnecessary components from the sample. Furthermore, a fourth reagent which is a buffer liquid and a fifth reagent containing a light emitting substrate are added to the relevant sample, and the mixed solution is stirred and warmed to prepare the reaction sample for measurement.

In such immune analyzing device, the light emitting amount generated by the reaction between the labeled antibody and the light emitting substrate after the complicating sample preparing steps is measured to quantitatively measure the antigen contained in the specimen that binds with the labeled antibody.

Japanese Laid-Open Patent Publication No. 6-160401 and Japanese Laid-Open Patent Publication No. 3-175361 disclose a device in which a specimen dispensing unit, a plurality of reagent dispensing units, a stirring device, a detecting unit etc. are arranged around a rotatable table holding a plurality of reaction containers, and the operation units of the specimen dispensing unit, the sample dispensing unit, the stirring device etc. are operated according to a predetermined sequence while rotating the rotatable table to perform the complicating sample preparing steps in each reaction container. The devices disclosed in the above publications are arranged with a plurality of container setting sections (driving devices) for setting the reaction container on the rotatable table or taking out the reaction container from the rotatable table, which container setting sections are arranged around the rotatable table.

U.S. Pat. No. 5,587,129 Publication discloses a blood coagulation analyzing device including a plurality of pipettes for dispensing the reagent for the specimens to perform coagulation reaction, a first rotatable table for holding the container accommodating the specimen and the container accommodating the reagent, a second rotatable table arranged with a warming device for warming the container accommodating the specimen at a predetermined temperature, an analyzing stage for optically detecting the degree of coagulation of the reaction sample prepared by adding reagent to the specimen warmed to the predetermined temperature, and a container distributing and supplying device arranged between the first rotatable table and the second rotatable table. In the relevant blood coagulation analyzing device, the container accommodating the specimen is transferred to the first rotatable table and the container accommodating the specimen is transferred to the second rotatable table by the container distributing and supplying device. In addition, a chucking finger positioned at one part of the circumference of the second rotatable table and on the upper part in the vertical direction of the analyzing stage to move in the front and back or left and right (X-Y) direction and to move in the up and down direction along the vertical direction is arranged in the blood coagulation analyzing device. The container accommodating the specimen is gripped from the second rotatable table by the chucking finger, and dispensed with reagent by the reagent dispensing unit and then stirred, and thereafter, the container is transferred to the analyzing stage.

However, in the devices disclosed in Japanese Laid-Open Patent Publication No. 6-160401 and Japanese Laid-Open Patent Publication No. 3-175361, the container setting section (driving device) for transferring the reaction container is arranged on the outer side of the rotatable table, only the reaction container conveyed to the vicinity of the container setting section with the rotation of the rotatable table can be transferred, and the destination of the reaction container is limited to the vicinity of the container setting section. Therefore, when transferring the reaction container among a plurality of positions of the rotatable table, the container setting section must be arranged in the vicinity of the relevant position, which enlarges the device and increases the cost. Furthermore, the processing sequence of the specimen is limited by the arrangement of the container setting section since only the reaction container positioned in the vicinity of the container setting section can be transferred. Therefore, the control of the rotatable table becomes complicating or measurement may not be possible for some items when measuring a plurality of items.

The chucking finger of the coagulation analyzing device disclosed in U.S. Pat. No. 5,587,129 is attached to the guide rails in the X-axis direction and the Y-axis direction arranged above one part of the second rotatable table and the analyzing stage. Thus, the chucking finger must move from the outside of the second rotatable table, hold the reaction container and transfer the same to the destination when transferring the reaction container on the second rotatable table, and thus the movement amount of the chucking finger is great.

It is conventionally known to analyze the substance to be analyzed using a solid phase reagent obtained by sensitizing the binding substance for the substance to be analyzed (antibody etc. for substance to be analyzed) in the liquid sample to solid phase and a labeled reagent. In this analysis, the liquid sample and the solid phase reagent are mixed and reacted, the solid phase bound with the substance to be analyzed (bound) and the other liquid (Free) are separated, the BF separating process of cleaning the separated solid phase is performed, and the amount of substance to be analyzed bound to the solid phase is measured.

The analyzing method described above includes a sandwich method in which a labeled reagent containing the binding substance different from the binding substance on the solid phase is bound to the substance to be analyzed bound to the binding substance on the solid phase, and a competitive method of competing the substance to be analyzed and the labeled reagent in binding to the solid phase, and the analyzing method corresponding to the substance to be analyzed is used.

The analyzing method described above is divided into two methods depending on the reaction step. The first method (two step assay method) is a method of performing the reaction process by mixing and reacting the liquid sample and the solid phase reagent, further mixing and reacting the labeled reagent, performing the BF separating process of separating into the solid phase bound with the substance to be analyzed and the labeled reagent (Bound) and the other liquid (Free) and cleaning and detecting the amount of label bound to the solid phase to analyze the substance in the liquid sample; and the second method (one step assay method) is a method of mixing and reacting the liquid sample, the reagent containing solid phase and the labeled reagent, performing the BF separating process of separating into the solid phase bound with the substance to be analyzed and the labeled reagent (Bound) and the other liquid (Free) and cleaning, and detecting the amount of label bound to the solid phase to analyze the substance in the liquid sample.

A method using the magnetic particles for the solid phase of the analyzing method involving the BF separating process is also known. An automatic analyzing device equipped with a dispensing mechanism for dispensing the sample and the magnetic particle reagent into the reaction container, a stirring mechanism for mixing the reacting container, a magnetism collecting mechanism for collecting the magnetic particles by contacting the magnet to the side wall of the reaction container subjected to reaction, a cleaning mechanism for suctioning the released sample in the magnetism collected state and injecting cleaning fluid, a stirring mechanism for stirring the reaction container injected with cleaning fluid, a dispensing mechanism for dispensing the labeled reagent, and a detecting mechanism for detecting the label is known as the automatic analyzing device for analyzing with the solid phase reagent using magnetic particles (see e.g., WO88/02866, Japanese Laid-Open Patent Publication No. 5-40122, Japanese Laid-Open Patent Publication No. 2002-168866).

The automatic analyzing device disclosed in WO88/02866 is configured so that the transfer disc of disc shape holding the reaction cell rotates and transfers the held reaction cell to the dispensing unit of the sample and the reagent, the reaction processing unit, the magnetic separating unit, the vibrating unit and the detecting unit at a predetermined timing. The magnetic separating unit is arranged at four locations, and at each magnetic separating unit, the BF separation of contacting the magnet to the side wall of the reaction cell to collect magnetism, and cleaning and removing the released sample is performed.

The automatic analyzing device disclosed in Japanese Laid-Open Patent Publication No. 5-40122 is configured so that when a linear reaction line holding the reaction cell with a belt is moved, the reaction cell on the reaction line is also moved to the dispensing unit of the sample and the reagent, the reaction processing unit, the BF separating unit and the detecting unit. In the BF separating unit, the magnet is contacted to the side wall of two reaction cells to collect magnetism, the released sample is cleaned and stirring is performed.

The automatic analyzing device disclosed in Japanese Laid-Open Patent Publication No. 2002-168866 includes a reaction table for holding the reaction cell, and is configured so that the cell conveying mechanism moves the reaction cell to the reaction processing position in the reaction table and the BF separating position. In the BF separating position, the magnet is simultaneously contacted to the side wall of six reaction cells and the BF separation of cleaning and removing the released sample is performed.

In such automatic analyzing devices, the BF separation is an important step, and the analyzing result greatly differs if the BF separation is insufficient. Thus, a configuration is provided so that magnetism collection is performed on the plurality of reaction cells to take enough time for magnetism collection.

However, in the automatic analyzing device disclosed in WO88/02866 Publication, all the reaction cells held at the transfer disc must be moved to move the target reaction to the reagent dispensing unit, the magnetism collecting unit and the stirring unit by rotating the transfer disc. In addition, in the automatic analyzing device disclosed in Japanese Laid Open Patent Publication No. 5-40122, the target reaction cells must be conveyed in order to the dispensing unit, the reaction processing unit and the BF separating unit. Furthermore, in the automatic analyzing device disclosed in Japanese Laid-Open Patent Publication No. 2002-168866, the BF separating unit must perform the BF separating process simultaneously on six reaction cells at a predetermined position of the reaction table. Thus, in these automatic analyzing devices, the measurement flow becomes complicating if the analyzing method and the reaction step must be changed depending on the measurement items, or the processing speed must be complied to the measurement items that require time in the reaction step if the reaction step includes both measurement items that require time and the measurement items that does not require time, and thus the processing speed is limited.

SUMMARY OF THE INVENTION

The scope of the present invention is defined solely by the appended claims, and is not affected to any degree by the statements within this summary.

An analyzing apparatus according to a first aspect of the present invention is an analyzing apparatus comprising: rotatable table arranged with a plurality of holes for accommodating the reaction container which includes a specimen and a reagent; and a container transferring section, arranged on the rotatable table, for transferring the reaction container.

A solid-liquid separation device according to a second aspect of the present invention is a solid-liquid separation device used in an analyzer for analyzing a target substance comprising: a holding part for holding a reaction container containing a reacted sample prepared by reacting a biological sample and a reagent containing magnetic particles for capturing a target substance in the biological sample; a collecting part for collecting the magnetic particles captured the target substance in the reaction container held by the holding part; a removing part for removing a residue other than the magnetic particles collected by the collecting part in the reaction container held by the holding part; a supplying part for supplying washing liquid into the reaction container removed the residue; and a stirring part for stirring the magnetic particles and the washing liquid under no collecting of the magnetic particles in the reaction container.

An analyzing apparatus according to a third aspect of the present invention is an analyzing apparatus comprising: a reaction processing unit for reacting a biological sample and a reagent containing magnetic particles for capturing a target substance in the biological sample in a reaction container; a separation processing unit comprises a holding part for holding the reaction container, a collecting part for collecting the magnetic particles captured the target substance in the reaction container held by the holding part and a removing part for removing a residue other than the magnetic particles collected by the collecting part in the reaction container held by the holding part; and a container transferring section comprises a gripping part for gripping the reaction container accommodating the reacted sample prepared by the reaction processing unit, a stirring part for stirring the reacted sample in the reaction container gripped by the gripping part and a moving part for moving the gripping part gripping the reaction container from the reaction processing unit to the separation processing unit.

A solid-liquid separation method according to a fourth aspect of the present invention is A solid-liquid separation method comprising the steps of: providing a reaction container containing a reaction product comprising magnetic particles captured a target substance and a residue other than the magnetic particles; collecting the magnetic particles in the reaction container; removing the residue in the reaction container under collecting the magnetic particles; releasing the collection of the magnetic particles; supplying washing liquid into the reaction container; stirring the magnetic particles and the washing liquid in the reaction container; collecting the magnetic particles in the reaction container; and removing the washing liquid in the reaction container.

DETAILED DESCRIPTION OF THE PREFERRED EMBODIMENTS

Figure 1:
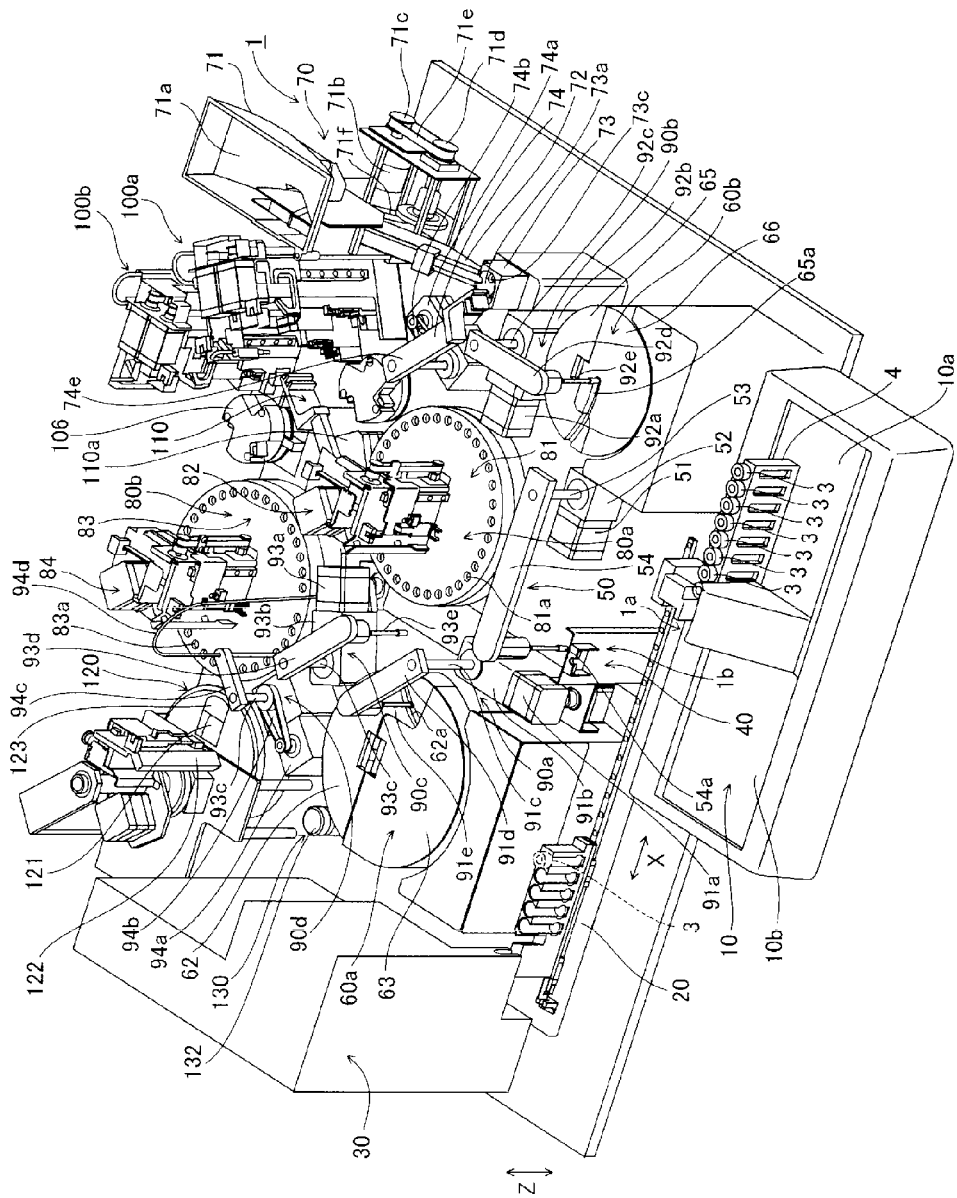
FIG. 1 is a perspective view showing the entire configuration of an immune analyzing device according to one embodiment of the present invention.
Figure 2:
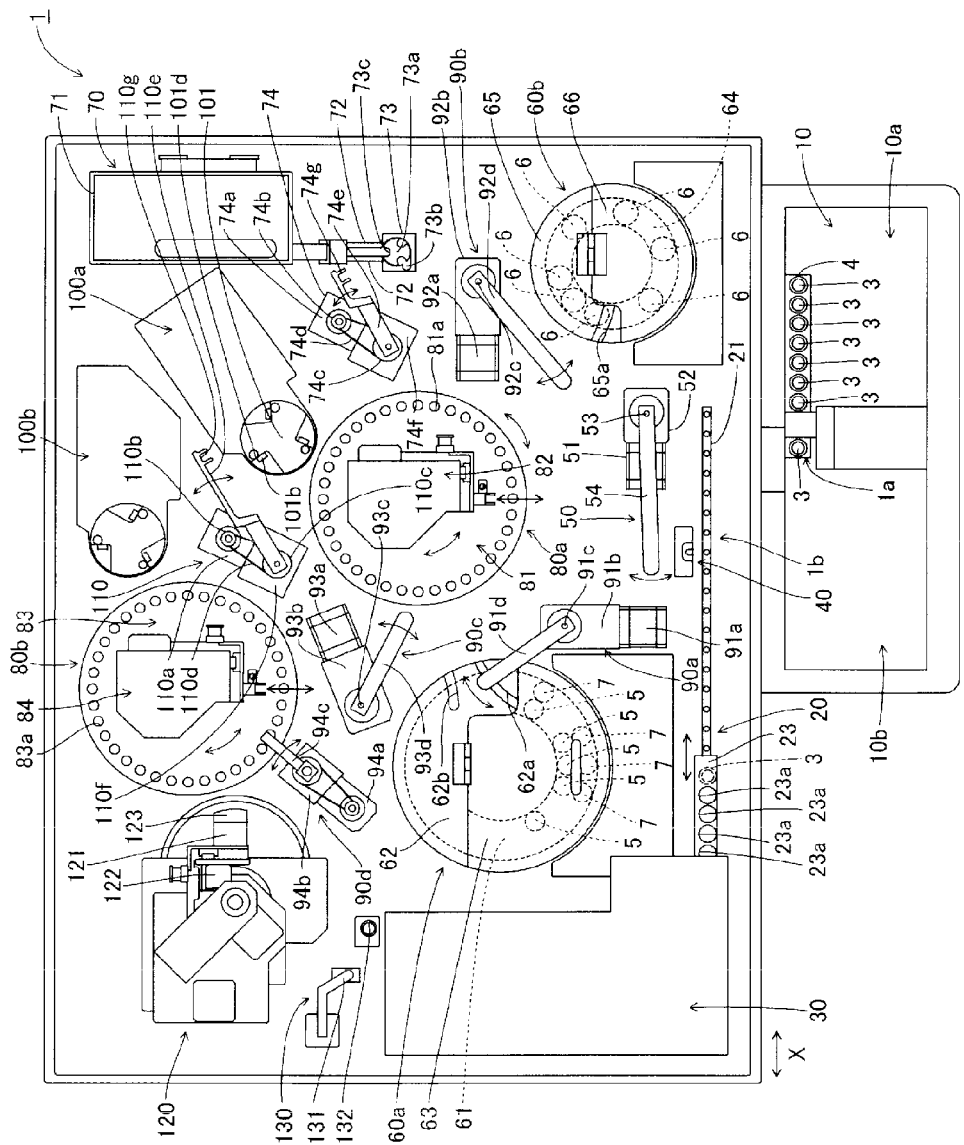
FIG. 2 is a plan view showing the entire configuration of the immune analyzing device according to the embodiment shown in FIG. 1.

The immune analyzing device 1 according to one embodiment of the present invention is a device for performing examination on various items such as hepatitis B, hepatitis C, tumor marker, thyroid hormone and the like using specimens such as blood. The immune analyzing device 1 is configured by a specimen conveying section (sampler) 10, an emergency specimen and chip conveying section 20, a pipette chip supply device 30, a specimen dispensing arm 50, reagent installing sections 61 and 62, a cuvette supply section 70, a primary reaction section 81 and a secondary reaction section 82, reagent dispensing arms 91, 92, 93 and 94, a BF separating section 101 and a BF separating section 102, a conveyance catcher 110, a detecting section 120, a disposing section 130, and a chip releasing section 140, as shown in FIGS. 1 and 2. In the immune analyzing device 1 according to the present embodiment, the disposable pipette chip 2 (see FIG. 2) is replaced each time suction and discharge of the specimen are performed to suppress the specimen such as blood suctioned and discharged by the specimen dispensing arm 50 from mixing with other specimen.

In the immune analyzing device 1, after the specimen such as blood containing antigen, which is the measurement target, trapped antibody (R1 reagent), magnetic particles (R2 reagent) are mixed, and the antigen, trapped antibody and magnetic particles are bound, the magnetic particles are attracted to a magnet 101*d* of the BF (Bound Free) separating section 101 thereby removing the solution containing non-reacting (Free) trapped antibody. After binding a labeled antibody (R3 reagent) to the magnetic particles bound with antigen, the bound magnetic particles, antigen, and labeled antibody are attracted to the magnet 102*d* of the BF separating section 102 thereby removing the R3 reagent containing the non-reacting (free) labeled antibody. Furthermore, after adding a light emitting substrate (R5 reagent) that emits light in the reaction process with the labeled antibody, the light emission amount produced by the reaction between the labeled antibody and the light emitting substrate is measured. The antigen contained in the specimen that binds with the labeled antibody is quantitatively measured through such process.

The specimen conveying section 10 is configured so as to convey a rack 4 mounted with a plurality of test tubes 3 accommodating the specimen to a position corresponding to the suction position 1*a* of the specimen dispensing arm 50, as shown in FIGS. 1 and 2. The specimen conveying section 10 includes a rack set part 10*a* for setting the rack 4 mounted with the test tube 3 accommodating non-processed specimens, and a rack storage part 10*b* for storing the rack 4 mounted with the test tube 3 accommodating the dispense processed specimens. When the test tube 3 accommodating the non-processed specimen is conveyed to the position corresponding to the suction position 1*a* of the specimen dispensing arm 50, the specimen such as blood in the test tube 3 is suctioned by the specimen dispensing arm 50 and the rack 4 mounted with the relevant test tube 3 is stored in the rack storage part 10*b*.

Figure 3:
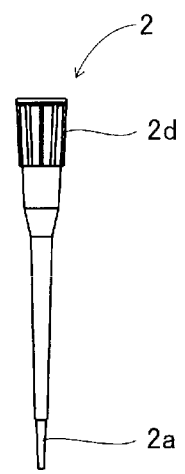
FIG. 3 is a front view of a pipette chip supplied by a pipette chip supplying device of the immune analyzing device according to the embodiment shown in FIG. 1.
Figure 5:
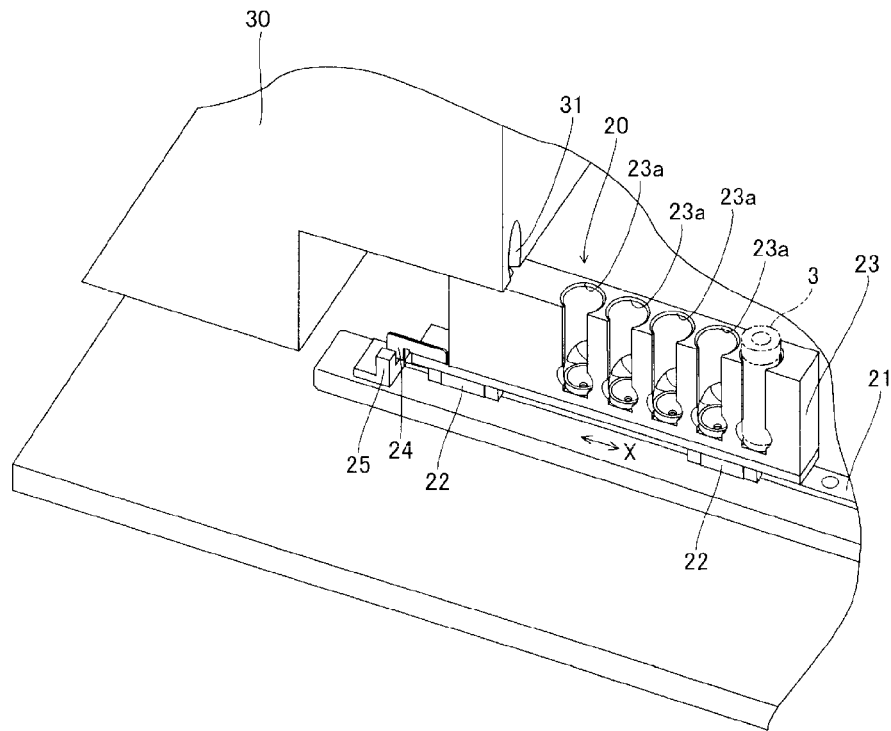
FIG. 5 is a perspective view showing an emergency specimen and chip conveying unit of the immune analyzing device according to the embodiment shown in FIG. 1.
Figure 6:
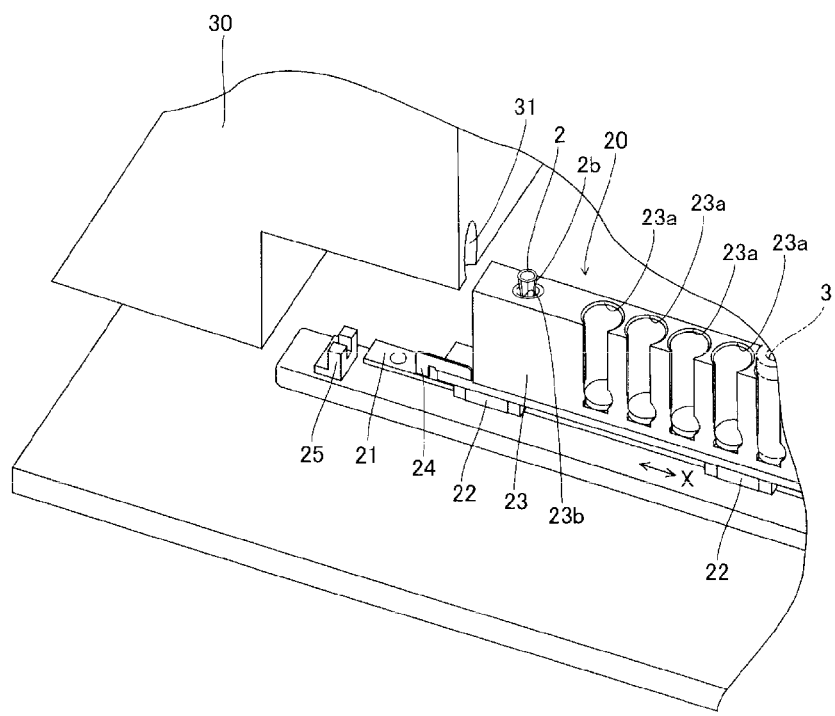
FIG. 6 is a perspective view showing an emergency specimen and chip conveying unit of the immune analyzing device according to the embodiment shown in FIG. 1.

The emergency specimen and chip conveying section 20 is configured so as to convey the test tube 3 accommodating emergency specimens, which must cut into the specimens being conveyed by the specimen conveying section 10 and examined, to an attachment position 1*b* of the specimen dispensing arm 50. As shown in FIGS. 5 and 6, the emergency specimen and chip conveying section 20 includes a slide rail 21 arranged so as to extend in the X direction, a linear moving guide including a slide main body 22 arranged movable along the slide rail 21, a conveying rack 23 attached to the slide main body 22, a detection strip 24 attached to the lower part of the conveying rack 23, and a light shielding sensor 25 light shielded by the detection strip 24. Furthermore, the conveying rack 23 is arranged with a test tube installing part 23*a* for installing the test tube 3 accommodating the emergency specimens, and a chip installing part 23*b* (see FIG. 6) of a long hole for mounting the pipette chip 2 (see FIG. 3) supplied from the pipette chip supply device 30 to be hereinafter described. The detection strip 24 is arranged so as to light shield the light shielding sensor 25 when arranged at a position of receiving the pipette chip 2 from the pipette chip supply device 30. The conveying rack 23 conveys the test tubes 3 accommodating the emergency specimens and the pipette chip 2 to the attachment position 1*b* (see FIGS. 1 and 2) of the specimen dispensing arm 50 by being moved along the slide rail 21 by the driving force from the motor (not shown).

In the present embodiment, the pipette chip supply device 30 has a function of installing one at a time the pipette chip (see FIG. 3) input to a chip refill section 31 to be hereinafter described to the chip installing part 23*b* of the conveying rack 23 of the emergency specimen and chip conveying section 20. Furthermore, the pipette chip supply device 30 also has a function of supplying the pipette chip to the chip installing part 23*b* of the conveying rack 23 with the distal end 2*a* (see FIG. 3) of the pipette chip 2 facing downward.

Figure 4:
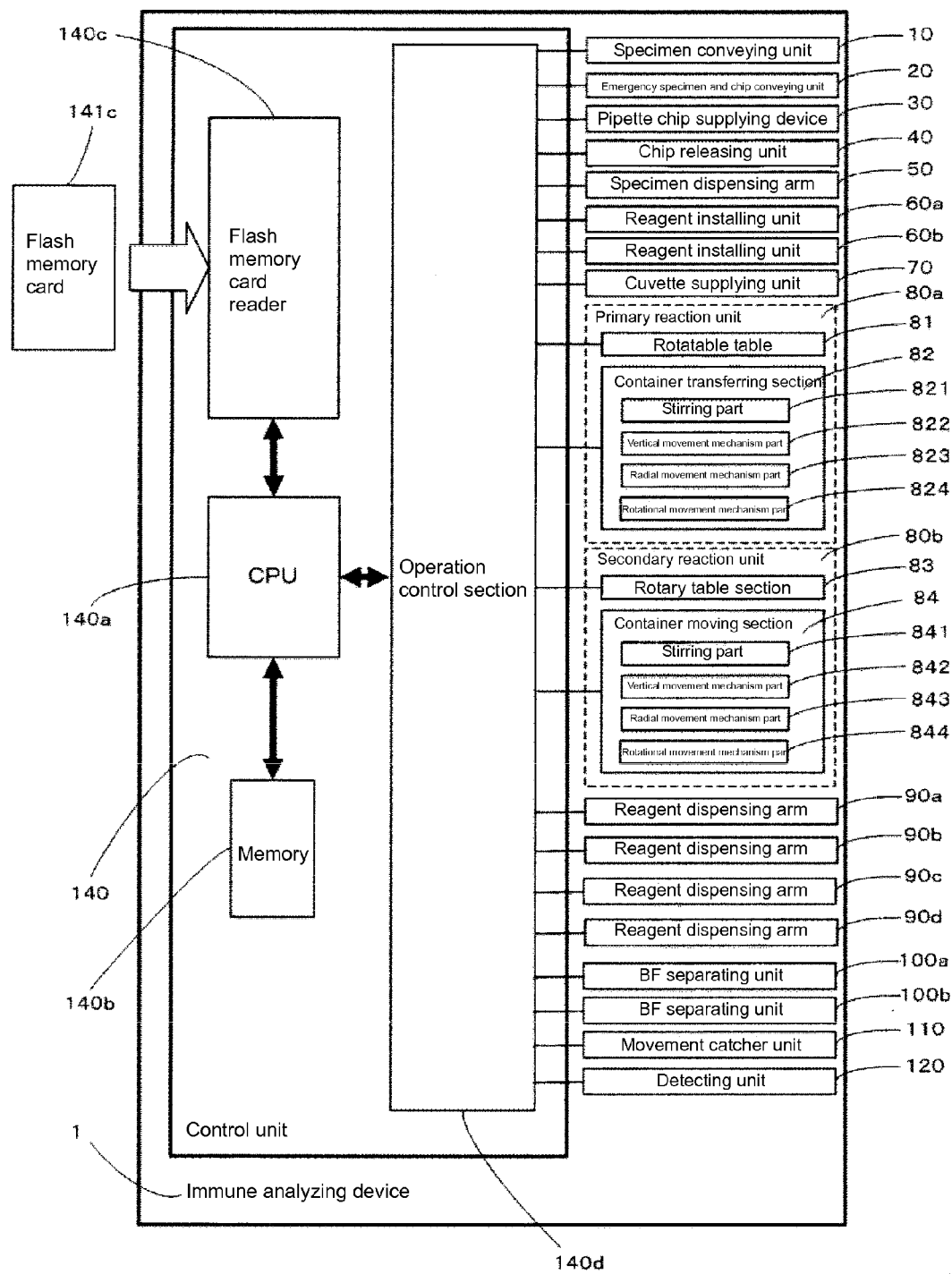
FIG. 4 is a block diagram showing the configuration of a control unit of the immune analyzing device according to the embodiment shown in FIG. 1.

The configuration of the control unit 140 will now be described. FIG. 4 is a block diagram showing the configuration of the control unit of the immune analyzing device 1. The control unit 140 includes a CPU 140*a*, a memory 140*b*, a flash memory card reader 140*c*, and an operation control section 140*d*. The CPU 140*a* and the memory 140*b*, the flash memory card reader 140*c* and the operation control section 140*d* are connected by way of a data transmission line to allow data transmission with each other. Thus, the CPU 140*a* reads and writes data with respect to the memory 140*b* and the flash memory card reader 140*c*, and transmits and receives data with respect to the operation control section 140*d*.

The CPU 140*a* can execute the computer program recorded on the memory 140*b* or the flash memory card 141*c*.

The memory 140*b* is configured by ROM and RAM, and is used to record computer program and data used for the execution thereof, and to read computer program and data. The memory 140*b* is also used as a work region of the CPU 140*a* and a storage region of the data when executing the computer program.

The flash memory card 140*c* is used in reading the data recorded on the flash memory card 141*c*. The flash memory card 141*c* includes a flash memory (not shown) so as to be able to hold the data even if power is not externally supplied. Furthermore, the computer program executed by the CPU 140*a* for controlling the operation of each unit of the above described immune analyzing device 1 is recorded on the flash memory card 141*c*.

The operation control section 140*d* includes a driver circuit for driving devices such as motor, electromagnetic valve, cooling device and the like. The operation control section 140*d* is electrically connected to each unit of the immune analyzing device 1 (specimen conveying unit (sampler) 10, emergency specimen and chip conveying unit 20, pipette chip supplying device 30, chip releasing unit 40, specimen dispensing arm 50, reagent installing units 60*a* and 60*b*, cuvette supplying unit 70, rotatable tables 81 and 83, container transferring sections 82 and 84, reagent dispensing arms 90*a*, 90*b*, 90*c*, and 90*d*, BF separating units 100*a* and 100*b*, a movement catcher unit 110, and a detecting unit 120) by way of electrical signal cable and the like. The operation control section 140*d* and each unit are thus able to transmit and receive electrical signals used in the operation control of the unit, and the operation control section 140*d* performs the operation control of each unit based on the program executed by the CPU 140*a*.

The operation of each unit is independently controlled by the control unit 140. That is, the control unit 140 transmits the operation command to each unit substantially at the same time, so that each unit is simultaneously operated. In the above described computer program, each unit can be controlled substantially at the same time so that each unit do not contact each other during the operation (e.g., so that the specimen dispensing arm 50 and the container transferring section 82 do not interfere during the operation).

The specimen conveying unit 10 is configured so as to convey a rack 4 mounted with a plurality of test tubes 3 accommodating the specimen to a position corresponding to the suction position 1*a* of the specimen dispensing arm 50, as shown in FIGS. 1 and 2. The specimen conveying unit 10 includes a rack setting section 10*a* for setting the rack 4 mounted with the test tube 3 accommodating non-processed specimens, and a rack storage section 10*b* for storing the rack 4 mounted with the test tube 3 accommodating the dispense processed specimens. When the test tube 3 accommodating the non-processed specimens is conveyed to the position corresponding to the suction position 1*a* of the specimen dispensing arm 50, the specimen such as blood in the test tube 3 is suctioned by the specimen dispensing arm 50 and the rack 4 mounted with the relevant test tube 3 is stored in the rack storage section 10*b*.

The emergency specimen and chip conveying unit 20 is configured so as to convey the test tube 3 accommodating emergency specimens, which must cut into the specimens being conveyed by the specimen conveying unit 10 to be examined, to an attachment position 1*b* of the specimen dispensing arm 50. As shown in FIGS. 5 and 6, the emergency specimen and chip conveying unit 20 includes a linear moving guide consisting of a slide rail 21 arranged so as to extend in the X direction and a slide main body 22 arranged movable along the slide rail 21; a conveying rack 23 attached to the slide main body 22; a detection strip 24 attached to the lower part of the conveying rack 23, and a light shielding sensor 25 light shielded by the detection strip 24. Furthermore, the conveying rack 23 is arranged with a test tube installing part 23*a* for installing the test tube 3 accommodating the emergency specimens, and a chip installing part 23*b* (see FIG. 6) of a long hole shape for mounting the pipette chip 2 (see FIG. 3) supplied from the shoot 31 of the pipette chip supplying device 30 to be hereinafter described. The detection strip 24 is arranged so as to light shield the light shielding sensor 25 when arranged at a position of receiving the pipette chip 2 from the pipette chip supplying device 30. The conveying rack 23 conveys the test tubes 3 accommodating the emergency specimens and the pipette chip 2 to the attachment position 1*b* (see FIGS. 1 and 2) of the specimen dispensing arm 50 by moving along the slide rail 21 by the driving force from the motor (not shown).

The pipette chip supplying device 30 has a function of installing one at a time the input pipette chip 2 (see FIG. 3) to the chip installing part 23*b* of the conveying rack 23 of the emergency specimen and chip conveying unit 20 by way of the shoot 31. The pipette chip supplying device 30 also has a function of passing the pipette chip 2 through the shoot 31 and supplying the pipette chip to the chip installing part 23*b* of the conveying rack 23 with the distal end 2*a* of the pipette chip 2 (see FIG. 3) facing downward.

Figure 7:
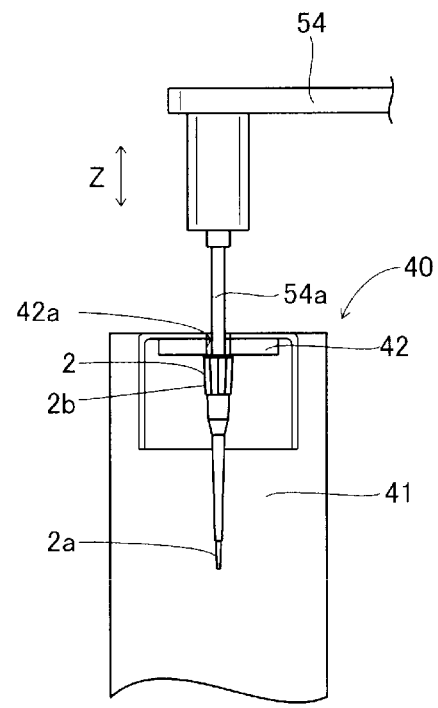
FIG. 7 is a front view showing a specimen dispensing arm and a chip releasing unit of the immune analyzing device according to the embodiment shown in FIG. 1.

The chip releasing unit 40 (see FIGS. 1 and 2) is arranged to release the pipette chip 2 (see FIG. 3) attached to the specimen dispensing arm 50 to be hereinafter described. The chip releasing unit 40 includes a steel plate 41 arranged so as to extend in the vertical direction (Z direction), and a release strip 42 made of resin attached to the steel plate 41, as shown in FIGS. 1 and 7. A cut-out portion 42*a* smaller than the diameter of the attachment part 2*b* (see FIG. 3) of the pipette chip 2 is formed in the release strip 42. When the specimen dispensing arm 50 is moved upward from a state in which the nozzle portion 54*a* of the specimen dispensing arm 50 is fitted to the cut-out portion 42*a* of the release strip 42, the lower surface of the release strip 42 of the chip releasing unit 40 and the upper surface of the attachment part 2*b* of the pipette chip 2 contact, and the pipette chip 2 releases from the arm section 54.

Figure 8:
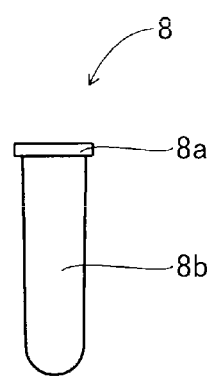
FIG. 8 is a front view of a cuvette supplied by a cuvette supplying device of the immune analyzing device according to the embodiment shown in FIG. 1.

The specimen dispensing arm 50 (see FIGS. 1 and 2) has a function of dispensing the specimen in the test tube 3 conveyed to the suction position 1*a* by the specimen conveying unit 10 to the cuvette 8 (see FIG. 8) accommodated in an accommodating hole 81*a* (see FIG. 9) of the rotatable table 81 of the primary reaction unit 80*a* to be hereinafter described. The specimen dispensing arm 50 includes a motor 51, a drive transmission part 52 connected to the motor 51, and the arm section 54 attached to the drive transmission part 52 by way of a shaft 53, as shown in FIGS. 1 and 2. The drive transmission part 52 is configured to turn the arm section 54 with the shaft 53 as the center and move the same in the vertical direction (Z direction) by the driving force from the motor 51. A nozzle portion 54*a* for suctioning and discharging the specimen is arranged at the distal end of the arm section 54. The pipette chip 2 (see FIG. 3) conveyed by the conveying rack 23 (see FIG. 6) of the emergency specimen and chip conveying unit 20 is attached to the distal end of the nozzle portion 54*a* (see FIG. 7).

A reagent installing section 60*a* (see FIGS. 1 and 2) includes an installing part 61 for installing the reagent bin 5 (see FIG. 2) accommodating the R1 reagent containing trapped antibody and the reagent bin 7 (see FIG. 2) accommodating the R3 reagent containing labeled antibody, an upper surface part 62 arranged at the upper part of the installing part 61 so that foreign materials such as dust do not enter the R1 reagent in the reagent bin 5 or the R3 reagent in the reagent bin 7 installed in the installing part 61, and a lid part 63 attached to the upper surface part 62 in an openable and closable manner. A groove part 62*a* to be inserted with a nozzle 91*e* of the reagent dispensing arm 90*a* to be hereinafter described, and a groove part 62*b* to be inserted with a nozzle 93*e* of the reagent dispensing arm 93*c* are formed in the upper surface part 62. The installing part 61 is rotatably configured so as to convey the installed reagent bin 5 and the reagent bin 7 to the position corresponding to the groove part 62*a* and the groove part 62*b* of the upper surface part 61*b*.

The reagent installing section 60*b* (see FIGS. 1 and 2) includes an installing part 64 for installing a reagent bin 6 accommodating the R2 reagent containing magnetic particles, an upper surface part 65 arranged at the upper part of the installing part 64 so that foreign materials such as dust do not enter the R2 reagent in the reagent bin 6 installed in the installing part 64, and a lid part 66 attached to the upper surface part 65 in an openable and closable manner. A groove part 65*a* to be inserted with a nozzle 92*e* of the reagent dispensing arm 90*b* to be hereinafter described is formed in the upper surface part 65. The installing part 64 is rotatably configured so as to convey the installed reagent bin 6 to a position corresponding to the groove part 65*a*.

A cuvette supplying unit 70 (see FIGS. 1 and 2) is configured so as to be able to sequentially supply a plurality of cuvettes 8 (see FIG. 8) to the accommodating hole 81*a* of the rotatable table 81 of the primary reaction section 80*a*. The cuvette supplying unit 70 includes a hopper feeder 71 capable of accommodating the plurality of cuvettes 8, two guiding plates 72 arranged below the hopper feeder 71, a supporting table 73 arranged at the lower end of the guiding plate 72, and a supply catcher section 74. The two guiding plates 72 are arranged parallel to each other at a distance smaller than the diameter of a collar 8*a* (see FIG. 8) of the cuvette 8 and larger than the diameter of a core 8*b* (see FIG. 8) of the cuvette 8. The hopper feeder 71 includes a hopper 71*a* capable accommodating the plurality of cuvettes 8, a motor 71*b* serving as a driving source, a main driving pulley 71*c* attached to the shaft of the motor 71*b*, a driven pulley 71*d* arranged at a predetermined distance from the main driving pulley 71*c*, a drive transmission belt 71*e* attached to the main driving pulley 71*c* and the driven pulley 71*d*, and an arm section 71*f* attached decentered with respect to the axis of the driven pulley 71*d*. Furthermore, the plurality of cuvettes 8 supplied to the hopper 71*a* of the hopper feeder 71 are stirred in the hopper 71*a* by the arm section 71*f* to be arrayed along the guiding plate 72 with the collar 8*a* engaging the upper surface of the two guiding plates 72. The supporting table 73 includes a rotating part 73*a* arranged rotatable with respect to the supporting table 73, and a concave part 73*b* (see FIG. 2) arranged so as to be adjacent to the rotating part 73*a*. In addition, three cut-out portions 73*c* are formed on the outer peripheral portion of the rotating part 73*a* at every predetermined angle (120° in the present embodiment). The cut-out portion 73*c* is arranged to accommodate the cuvette 8 guided by the guiding plate 72 one by one. Furthermore, the concave part 73*b* is configured so as to receive the cuvette 8 rotated while being accommodated in the cut-out portion 73*c* of the rotating part 73*a*.

The supply catcher section 74 (see FIGS. 1 and 2) has a function of transferring the cuvette 8 (see FIG. 8) received by the concave part 73*b* to the accommodating hole 81*a* of the rotatable table 81 of the primary reaction unit 80*a*, as shown in FIGS. 1 and 2. The supply catcher section 74 includes a motor 74*a*, a main driving pulley 74*b* connected to the motor 74*a*, a driven pulley 74*c* arranged at a predetermined distance from the main driving pulley 74*b*, a drive transmission belt 74*d* attached to the main driving pulley 74*b* and the driven pulley 74*c*, an arm section 74*e* attached to the driven pulley 74*c* by way of a shaft, and a driving part 74*f* for moving the arm section 74*e* in the vertical direction. A chuck part 74*g* for sandwiching and gripping the cuvette 8 is arranged at the distal end of the arm section 74*e*.

Figure 9:
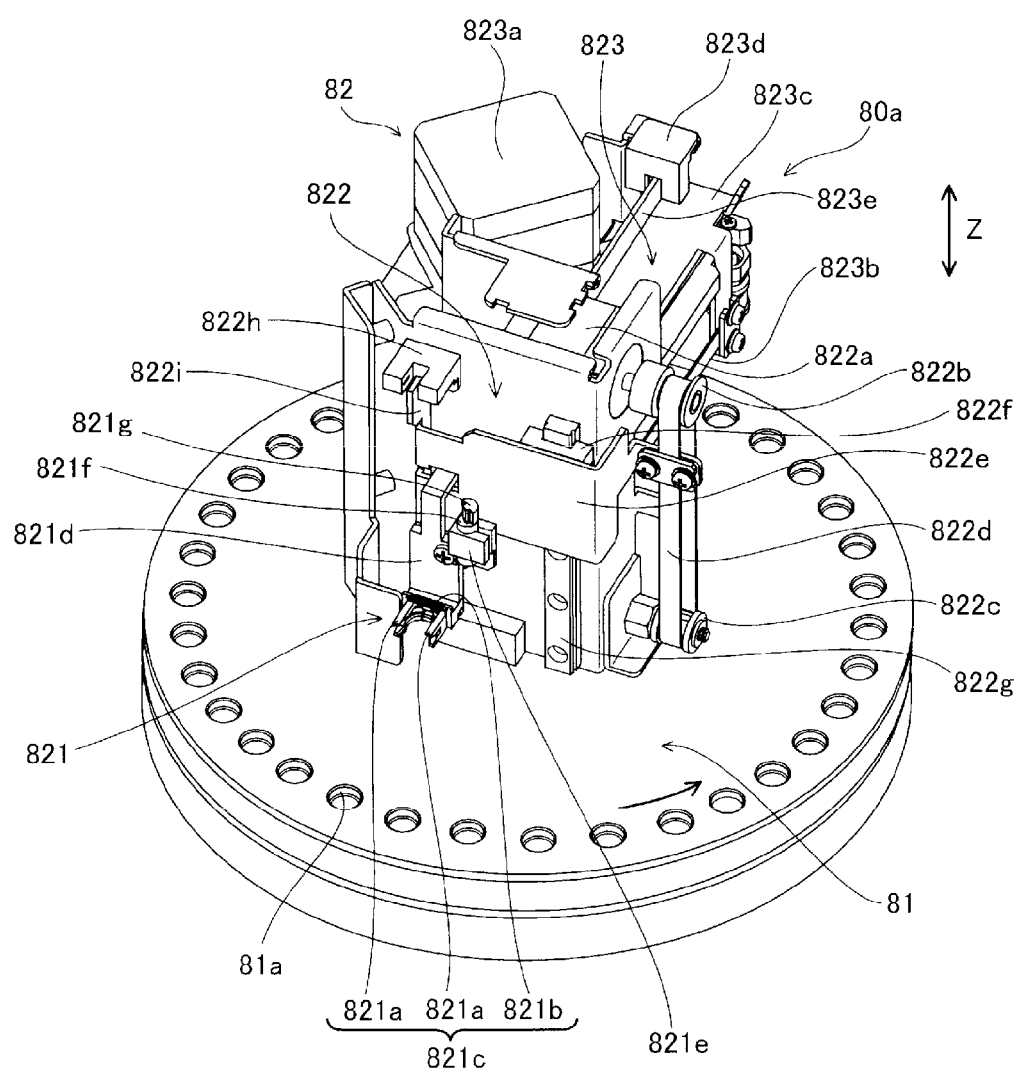
FIG. 9 is a perspective view showing a primary reaction unit of the immune analyzing device according to the embodiment shown in FIG. 1.

The primary reaction unit 80*a* is arranged to rotatably transfer the cuvette 8 accommodated in the accommodating hole 81*a* arranged in pluralities in a circular ring shape on the rotatable table 81 by a predetermined angle at every predetermined period (18 seconds in the present embodiment), and to stir the specimen, R1 reagent and the R2 reagent in the cuvette 8, as shown in FIG. 9. That is, the primary reaction unit 80*a* is arranged to react the R2 reagent containing magnetic particles and the antigen in the specimen in the cuvette 8. The primary reaction unit 80*a* is configured by a rotatable table 81 for conveying the cuvette 8 accommodating the specimen, the R1 reagent, and the R2 reagent in the rotating direction, and a container transferring section 82 for stirring the specimen, R1 reagent, and R2 reagent in the cuvette 8 and transferring the cuvette 8 accommodating the stirred specimen, the R1 reagent and the R2 reagent to the BF separating unit 100*a* (see FIGS. 1 and 2) to be hereinafter described.

The rotatable table 81 has a circular upper surface, and the plurality of accommodating holes 81*a* are formed in the upper surface at equidistance so as to form a circular ring coaxially with the circle. The rotatable table 81 is configured so as to rotatably transfer the cuvette 8 held in the accommodating hole 81*a* by a predetermined angle every 18 seconds. Thus, various devices (specimen dispensing arm 50, reagent dispensing arms 90*a* and 92 etc.) of the immune analyzing device 1 are controlled so as to operate on the cuvette 8 at the predetermined transferred position at a timing transferred to the predetermined position by the rotatable table 81.

The container transferring section 82 is rotatably arranged at the central portion of the rotatable table 81. The container transferring section 82 has a function of gripping the cuvette 8 accommodated in the accommodating hole 81*a* of the rotatable table 81 and stirring the sample in the cuvette 8. Furthermore, the container transferring section 82 has a function of transferring the cuvette 8 accommodating the sample obtained by stirring and incubating the specimen, the R1 reagent and the R2 reagent to the BF separating unit 100*a* (see FIGS. 1 and 2). The container transferring section 82 is configured by a stirring part 821 for gripping and stirring the cuvette 8, a vertical movement mechanism part 822 for moving the stirring part 821 in the vertical direction, a radial movement mechanism part 823 for moving the stirring part 821 and the vertical movement mechanism part 822 to the outer side from the center of the rotatable table 81, and a rotational movement mechanism part 824 (see FIG. 10), as shown in FIG. 9.

The stirring part 821 includes a chuck portion 821*c* consisting of a pair of plate members 821*a* for gripping the core 8*b* (see FIG. 8) of the cuvette 8 and a coil spring 821*b* bridged across the pair of plate members 821*a*, a supporting member 821*d* for supporting the chuck portion 821*c*, a motor 821*f* attached to a motor attachment portion 821*e* integrally arranged at the supporting member 821*d*, and an eccentric weight 821*g* rotatably attached to the shaft of the motor 821*f*. Therefore, the cuvette 8 arranged between the plate members 821*a* of the chuck portion 821*c* is gripped by the biasing force of the coil spring 821*b*. The sample in the cuvette 8 is stirred when the motor 821*f* is driven with the cuvette 8 gripped by the chuck portion 821*c*. Specifically, when the motor 821*f* is driven, the eccentric weight 821*g* rotates and the eccentric weight 821*g* and the motor 821*f* swings and vibrates. The vibration of the eccentric weight 821*g* and the motor 821*f* is transmitted to the cuvette 8 gripped at the chuck portion 821*c*, and the sample in the cuvette 8 is stirred.

The vertical movement mechanism part 822 is arranged at the movement member 323*c* of the radial movement mechanism part 823, and is configured to be movable in the radial direction of the rotatable table 81 integrally with the radial movement mechanism part 823. The vertical movement mechanism part 822 is configured by a motor 822*a* serving as a driving source, a main driving pulley 822*b* connected to the motor 822*a*, a driven pulley 822*c* arranged at a predetermined distance from the main driving pulley 822*b*, a drive transmission belt 822*d* attached to the main driving pulley 822*b* and the driven pulley 822*c*, a movement member 822*e* connected to the drive transmission belt 822*d*, a linear moving guide consisting of a slide main body 822*f* attached to the movement member 822*e* and a slide rail 822*g* attached to the radial movement mechanism part 823 to be hereinafter described, and a light shielding sensor 822*h*. A detection strip 822*i* detected by the light shielding sensor 822*h* is integrally formed at the movement member 822*e*. The stirring part 821 is arranged on the movement member 822*e*. Therefore, when the motor 822*a* is driven, the drive transmission belt 822*d* is driven by way of the main driving pulley 822*b*, and the movement member 822*e* connected to the drive transmission belt 822*d* is moved in the vertical direction (Z direction). The stirring part 821 arranged at the movement member 822*e* is thereby moved in the vertical direction, and the cuvette 8 gripped by the chuck portion 821*c* of the stirring part 821 can be moved in the vertical direction.

The radial movement mechanism part 823 is configured by a motor 823*a* serving as a driving source, a drive transmission belt 823*b* driven with the drive of the motor 823*a*, a movement member 823*c* connected to the drive transmission belt 823*b*, a linear moving guide (not shown) for moving the movement member 823*c* towards the outer side from the center of the rotatable table 81, and a light shielding sensor 823*d*. A detection strip 823*e* detected by the light shielding sensor 823*d* is arranged on the movement member 823*c*. Therefore, when the motor 823*a* is driven, the drive transmission belt 823*b* is driven, and the movement member 823*c* connected to the drive transmission belt 823*b* is moved in the radial direction of the rotatable table 81. Thus, the vertical movement mechanism part 822 arranged at the movement member 823*c* is thus moved in the radial direction of the rotatable table 81, and the stirring part 821 arranged at the movement member 822*e* of the vertical movement mechanism part 822 is moved in the radial direction of the rotatable table 81.

Figure 10:
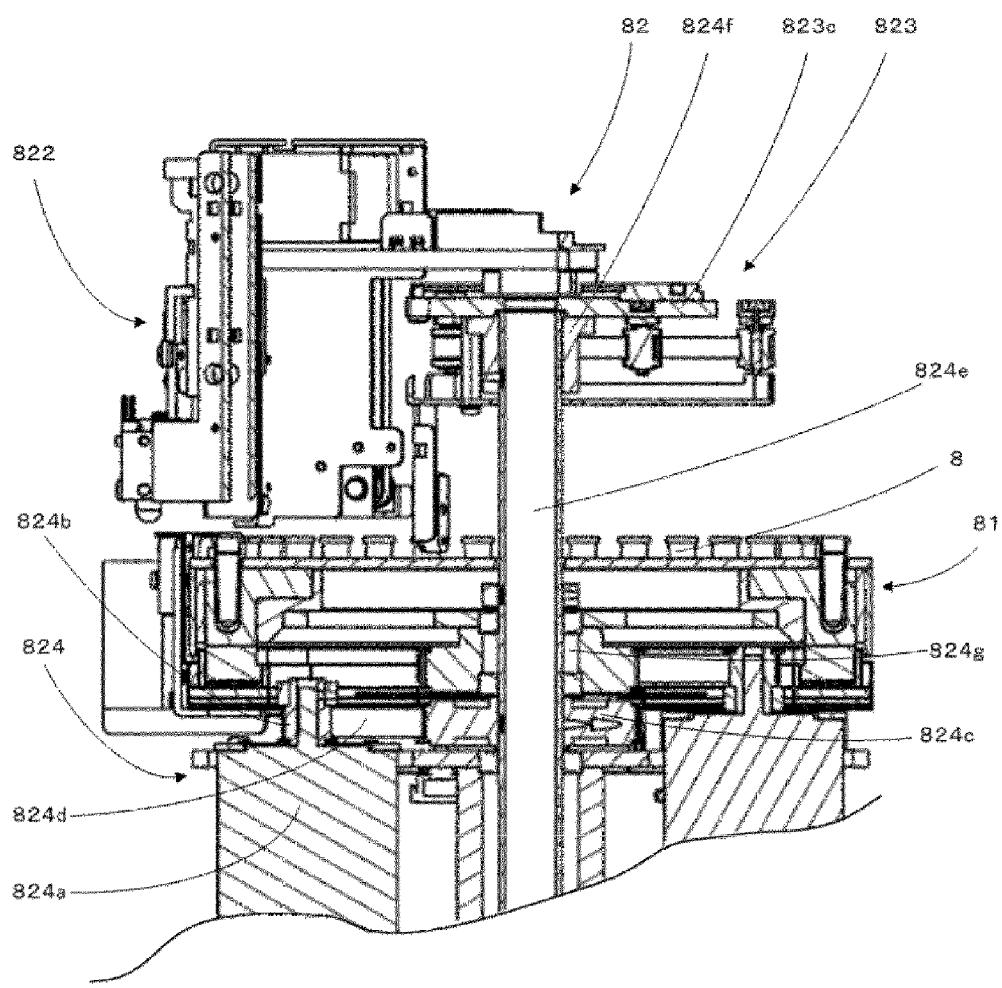
FIG. 10 is a cross sectional view showing the primary reaction unit of the immune analyzing device according to the embodiment shown in FIG. 1.

FIG. 10 is a cross sectional side view showing the configuration of the primary reaction unit of the immune analyzing device according to one embodiment shown in FIG. 1. As shown in FIG. 10, the rotational movement mechanism part 824 is configured by a motor 824*a* serving as a driving source, a main driving pulley 824*b* connected to the motor 824*a*, a driven pulley 824*c* arranged at a predetermined distance from the main driving pulley 824*b*, a drive transmission belt 824*d* attached to the main driving pulley 824*b* and the driven pulley 824*c*, a rotating shaft 824*e* fixedly attached to the driven pulley 824*c*, and a fixed member 824*f* fixedly attached at the upper end of the rotating shaft 824*e*. The rotating shaft 824*e* is supported in a freely rotating manner by the bearing 824*g* attached at the center of the rotatable table 81, and is relatively rotated with respect to the rotatable table 81. Furthermore, the fixed member 824*f* is fixed at the lower part of the above described movement member 823*c*. The vertical movement mechanism part 822 and the radial movement mechanism part 823 are fixed and supported at the upper end of the rotating shaft 824*e* by way of the fixed member 824*f*, and the other portions of the vertical movement mechanism part 822 and the radial movement mechanism part 823 do not contact other units such as the rotatable table 81. Therefore, when the motor 824*a* is operated, the drive transmission belt 824*d* is driven by way of the main driving pulley 824*b* and the rotating force is transmitted to the rotating shaft 824*e* by way of the driven pulley 824*c*, whereby the rotating shaft 834*e* relatively rotates with respect to the rotatable table 81. The movement member 823*c* fixed to the rotating shaft 824*e* by the fixed member 824*f* integrally rotates with the rotating shaft 824*e*. The vertical movement mechanism part 822 and the radial movement mechanism part 823 thus rotate in the circumferential direction of the rotatable table 81.

The reagent dispensing arm 90*a* (see FIGS. 1 and 2) has a function of suctioning the R1 reagent in the reagent bin 5 installed in the installing part 61 of the reagent installing unit 60*a* and dispensing the suctioned R1 reagent into the cuvette 8 dispensed with the specimen of the primary reaction unit 80*a*. The reagent dispensing arm 90*a* includes a motor 91*a*, a drive transmission part 91*b* connected to the motor 91*a*, and an arm section 91*d* attached to the drive transmission part 91*b* by way of a shaft 91*c*. The drive transmission part 91*b* is configured so as to turn the arm section 91*d* with the shaft 91*c* as the center and move the same in the vertical direction by the driving force from the motor 91*a*. A nozzle 91*e* for suctioning and discharging the R1 reagent in the reagent bin 5 is attached to the distal end of the arm section 91*d*. That is, the nozzle 91*e* suctions the R1 reagent in the reagent bin 5 through the groove part 62*a* of the upper surface 62 of the reagent installing unit 60*a*, and thereafter, the suctioned R1 reagent is dispensed into the cuvette 8 dispensed with the specimen.

The reagent dispensing arm 90*b* (see FIGS. 1 and 2) has a function of dispensing the R2 reagent in the reagent bin 6 installed at the installing part 64 of the reagent installing unit 60*b* into the cuvette 8 dispensed with the specimen and the R1 reagent of the primary reaction unit 80*a*. The reagent dispensing arm 90*b* includes a motor 92*a*, a drive transmission part 92*b* connected to the motor 92*a*, and an arm section 92*d* attached to the drive transmission part 92*b* by way of a shaft 92*c*. The drive transmission part 92*b* is configured to turn the arm section 92*d* with the shaft 92*c* as the center and move the same in the vertical direction (Z direction) by the driving force from the motor 92*a*. A nozzle 92*e* for suctioning and discharging the R2 reagent in the reagent bin 6 is attached to the distal end of the arm section 92*d*. That is, the nozzle 92*e* suctions the R2 reagent in the reagent bin 6 through the groove part 65*a* of the upper surface 65 of the reagent installing unit 60*b*, and thereafter, the suctioned R2 reagent is dispensed into the cuvette 8 dispensed with the specimen.

Figure 11:
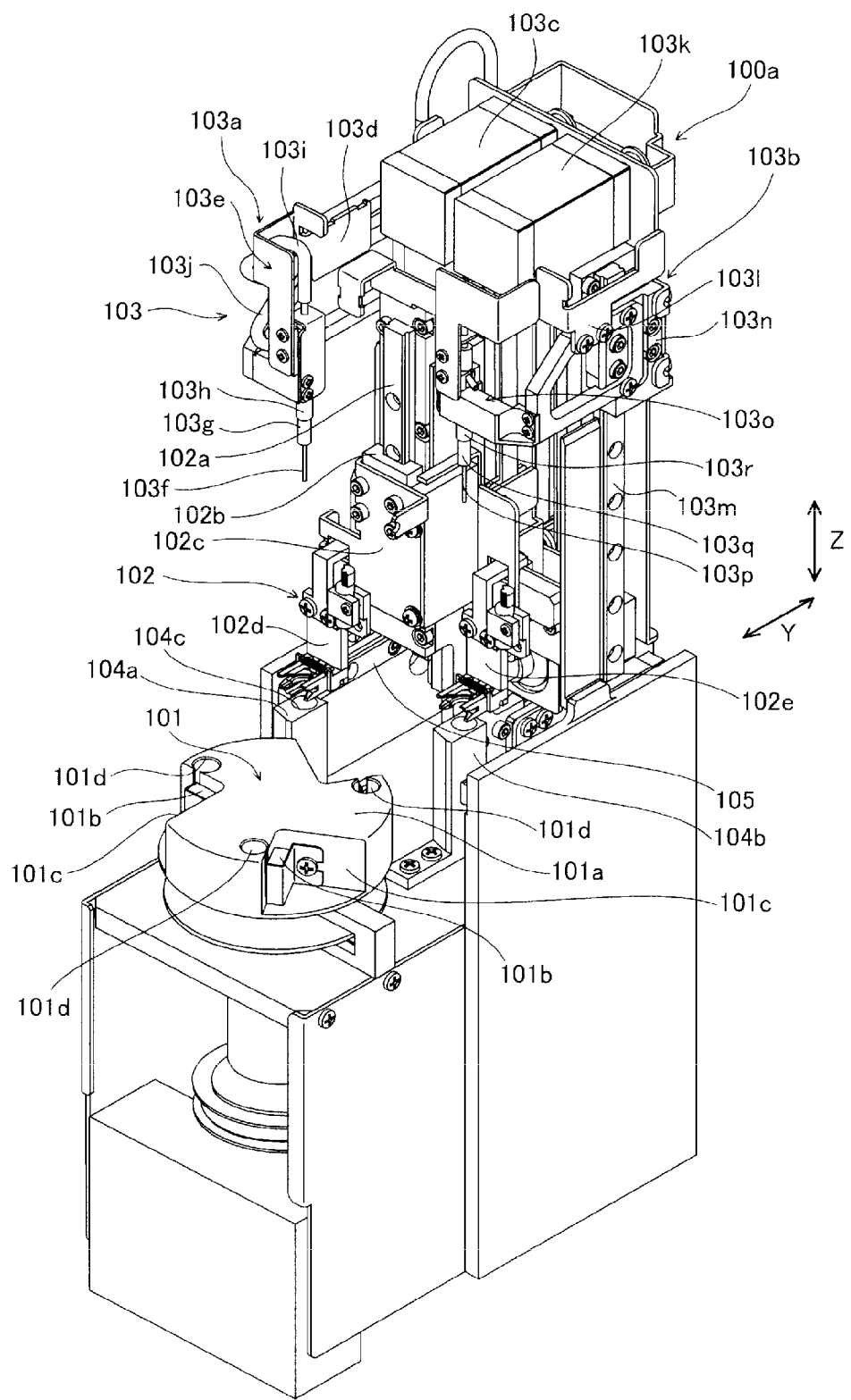
FIG. 11 is a perspective view showing a BF separating unit of the immune analyzing device according to the embodiment shown in FIG. 1.

In the present embodiment, the BF separating unit 100*a* (see FIGS. 1 and 2) is arranged to separate the non-reacting R1 reagent (unnecessary component) and the magnetic particles from the sample in the cuvette 8 (see FIG. 8) transferred by the container transferring section 82 of the primary reaction unit 80*a*. As shown in FIG. 11, the BF separating unit 100*a* includes a magnetism collecting section 101 for installing the cuvette 8 and transferring the same in the rotating direction, a stirring mechanism section 102 for stirring the sample in the cuvette 8, a separating mechanism section 103 for suctioning the sample in the cuvette 8 and discharging the cleaning fluid, and nozzle cleaning sections 104*a* and 104*b*.

In the present embodiment, the magnetism collecting section 101 includes an installing part 101*a* configured in a rotatable manner, and three magnets 101*b* for collecting the magnetic particles in the cuvette 8. Three concave parts 101*c*, and three cuvette installing holes 101*d* arranged at an interval of 120 degrees so as to be adjacent to the concave part 101*c* are formed in the installing part 101*a*. The three magnets 101*b* are attached to the concave part 101*c* so as to be positioned on the side of the cuvette 8 arranged in the cuvette installing hole 101*d*. In the present embodiment, the magnetism collecting section 101 is rotated by 120 degrees, so that the cuvettes 8 installed in the three installing holes 101*d* can be moved to a position corresponding to the nozzle portion 103*f* of a primary separating part 103*a* and the nozzle portion 103*p* of a secondary separating part 103*b*.

The stirring mechanism section 102 is arranged to be movable in the front and back direction along the slide rail 105 extending in the front and back direction (Y direction).

The stirring mechanism section 102 is configured by a linear moving guide consisting of a slide rail 102a extending in the vertical direction (Z direction) and a slide main body 102b, a movement member 102c attached to the slide main body 102b, and a primary stirring part 102d and a secondary stirring part 102e attached to the movement member 102c. That is, the primary stirring part 102d and the secondary stirring part 102e integrally move in the vertical direction along the slide rail 102a.

Figure 12:
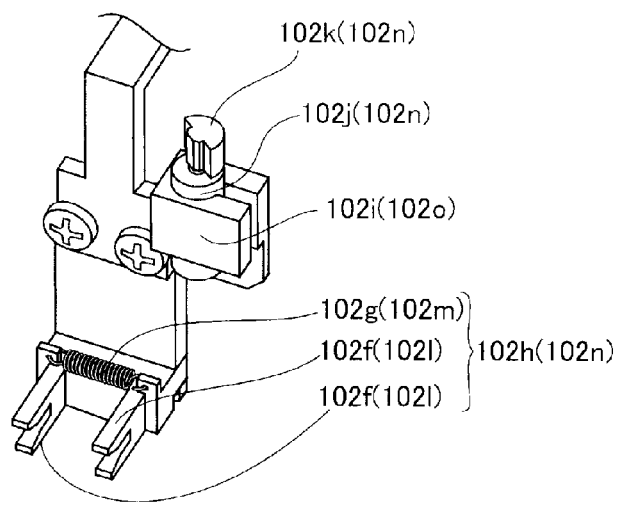
FIG. 12 is a perspective view showing a stirring part of the BF separating unit of the immune analyzing device according to the embodiment shown in FIG. 1.
Figure 13:
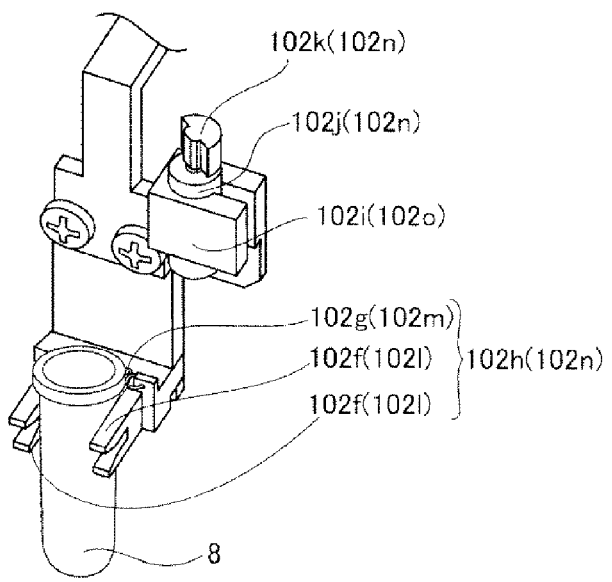
FIG. 13 is a cross sectional view showing the stirring part of the BF separating unit of the immune analyzing device according to the embodiment shown in FIG. 1.

In the present embodiment, the primary stirring part 102d has a function of lifting the cuvette 8 arranged in the cuvette installing hole 101d of the magnetism collecting section 101 and stirring the same in the non-magnetism collected state. The primary stirring part 102d includes a chuck portion 102h made up of a pair plate members 102f for gripping the cuvette 8 and a coil spring 102g bridged across the pair of plate members 102f, a motor supporting portion 102i arranged in the movement member 102c (see FIG. 11), a motor 102j supported at the motor supporting portion 102i, and an eccentric weight 102k attached to the shaft of the motor 102j, as shown in FIGS. 12 and 13. Furthermore, the secondary stirring part 102e has a configuration similar to the primary stirring part 102d and has a function of lifting the cuvette 8 arranged in the cuvette installing hole 101d of the magnetism collecting section 101 (see FIG. 11) and stirring the same in the non-magnetism collected state. The secondary stirring part 102e includes a chuck portion 102n made up of the pair of plate members 102l and a coil spring 102m, a motor supporting portion 102o, a motor 102p, and an eccentric weight 102q.

Furthermore, as shown in FIG. 11, the separating mechanism section 103 is arranged movable in the front and back direction (Y direction) along the slide rail 105 independent from the stirring mechanism section 102. That is, the stirring mechanism section 102 and the separating mechanism section 103 move in the front and back direction along a common slide rail 105, and thus the separating mechanism section 103 cannot move forward unless the stirring mechanism section 102 moves forward, and the stirring mechanism section 102 cannot move backward unless the separating mechanism section 103 moves backward. The separating mechanism section 103 includes a primary separating part 103a and a secondary separating part 103b, which primary separating part 103a and secondary separating part 103b are movable in the vertical direction independent to each other.

Figure 14:
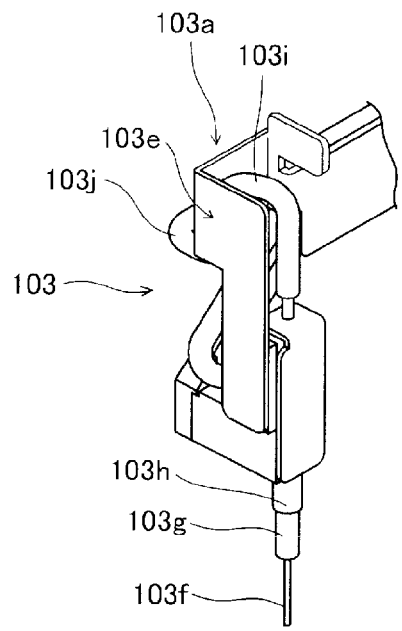
FIG. 14 is an enlarged perspective view showing a cleaning part of the BF separating unit of the immune analyzing device according to the embodiment shown in FIG. 1.

The primary separating part 103a includes a motor 103c, a movement member 103d that moves with the drive of the motor 103c, a linear moving guide (not shown) and a primary cleaning part 103e. The primary cleaning part 103e has a function of supplying cleaning fluid to the cuvette 8 arranged in the cuvette installing hole 101d of the magnetism collecting section 101 and discharging the same. In the present embodiment, the primary cleaning part 103e includes a discharging part 103g including a nozzle portion 103f for suctioning the unnecessary components of the cuvette 8, and a supplying part 103h for supplying cleaning fluid to the cuvette 8 through a path different from the path through which the unnecessary component suctioned by the nozzle portion 103 pass, as shown in FIG. 14. Furthermore, the unnecessary component suctioned by the nozzle portion 103f is discharged through a tube 103i connected to the nozzle portion 103f, and the cleaning fluid is supplied to the supplying part 103h through a tube 103j from a tank (not shown) and the like arranged at the lower part of the immune analyzing device 1.

The secondary separating part 103b has the same configuration as the primary separating part 103a. That is, the secondary separating part 103b also includes a motor 103k, a movement member 103l, a linear moving guide consisting of a slide rail 103m and a slide main body 103n, and a secondary cleaning part 103o, as shown in FIG. 11. The secondary cleaning part 103o also has the same configuration as the primary cleaning part 103e of the primary separating part 103a and includes a discharging part 103q with a nozzle portion 103p and a supplying part 103r.

Figure 15:
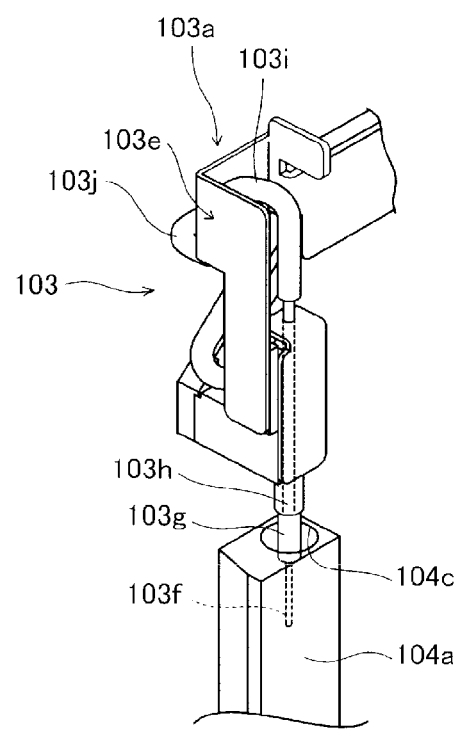
FIG. 15 is an enlarged perspective view showing the cleaning part and a nozzle cleaning section of the BF separating unit of the immune analyzing device according to the embodiment shown in FIG. 1.

The nozzle cleaning section 104a is arranged to clean the nozzle portion 103f of the primary separating part 103a. Specifically, as shown in FIG. 15, the nozzle cleaning section 104a includes a hole 104c through which the nozzle portion 103f can be inserted, and when the cleaning fluid is supplied from the supplying part 103h with the nozzle portion 103f inserted into the hole 104c of the nozzle cleaning section 104a, the cleaning fluid flows along the nozzle portion 103f and is discarded to the nozzle cleaning section 104a. The unnecessary component including the specimen and the R1 reagent attached to the nozzle portion 103f is thus rinsed away by the cleaning fluid supplied from the supplying part 103h. As a result, the unnecessary component of the previous cuvette 8 is suppressed from being carried on if the nozzle portion 103f is inserted into the next cuvette 8. The nozzle cleaning section 104b also has a similar function as the nozzle cleaning section 104a, and is arranged to clean the nozzle portion 103p of the secondary separating part 103b.

The movement catcher unit 110 (see FIGS. 1 and 2) has a function of transferring the cuvette 8 (see FIG. 8) of the magnetism collecting section 101 of the BF separating unit 100a separated from the non-reacting R1 reagent and the like to the holding part 83a of the rotatable table 83 of the secondary reaction unit 80b. The movement catcher unit 110 includes a motor 110a, a main driving pulley 110b connected to the motor 110a, a driven pulley 110d arranged at a predetermined distance from the main driving pulley 110b, a drive transmission belt 110d attached to the main driving pulley 110b and the driven pulley 110c, and an arm section 110e attached to the driven pulley 110c by way of a shaft, and a driving part 110f for moving the arm section 110e in the vertical direction. In addition, a chuck portion 110g for sandwiching and gripping the cuvette 8 is arranged at the distal end of the arm section 110e.

The secondary reaction unit 80b (see FIGS. 1 and 2) has a configuration similar to the primary reaction unit 80a, and is arranged to rotatably transfer the cuvette 8 accommodated in the holding part 83a of the rotatable table 83 by a predetermined angle at every predetermined period (18 seconds in the present embodiment), and to stir the specimen, R1 reagent, R2 reagent, R3 reagent and R5 reagent in the cuvette 8. That is, the secondary reaction unit 80b is arranged to react the R3 reagent containing labeled antibody and the antigen in the specimen, and to react the R5 reagent containing light emitting substrate and the labeled antibody of the R3 reagent in the cuvette 8. The secondary reaction unit 80b is configured by a rotatable table 83 for transferring the cuvette 8 accommodating the specimen, the R1 reagent, and the R2 reagent, R3 reagent and the R5 reagent in the rotating direction, and a container transferring section 84 for stirring the specimen, R1 reagent, R2 reagent, R3 reagent and R5 reagent in the cuvette 8, and transferring the cuvette 8 accommodating the stirred specimen and the like to the BF separating unit 100b to be hereinafter described. Furthermore, the container transferring section 84 has a function of transferring the cuvette 8 processed by the BF separating unit 100b again to the holding part 83a of the rotatable table 83. The detailed configuration of the secondary reaction unit 80b is the same as the primary reaction unit 80a, and thus the description thereof will be omitted.

The reagent dispensing arm 90c (see FIGS. 1 and 2) has a function of suctioning the R3 reagent in the reagent bin 7 installed in the installing part 61 of the reagent installing unit 60a and dispensing the suctioned R3 reagent into the cuvette 8 dispensed with the specimen, the R1 reagent and the R2 reagent of the primary reaction unit 80a. The reagent dispensing arm 90c includes a motor 93a, a drive transmission part 93b connected to the motor 93a, and an arm section 93d attached to the drive transmission part 93b by way of a shaft 93c. The drive transmission part 93b is configured so as to turn the arm section 93d with the shaft 93c as the center and move the same in the vertical direction by the driving force from the motor 93a. Furthermore, a nozzle 93e for suctioning and discharging the R3 reagent in the reagent bin 7 is attached to the distal end of the arm section 93d. That is, the nozzle 93e suctions the R3 reagent in the reagent bin 7 through the groove part 62a of the upper surface 62 of the reagent installing unit 60a, and thereafter, the suctioned R3 reagent is dispensed into the cuvette 8 dispensed with the specimen, the R1 reagent, and the R2 reagent.

The BF separating unit 100b (see FIGS. 1 and 2) has a configuration similar to the BF separating unit 100a, and is arranged to separate the non-reacting R3 reagent (unnecessary component) and the magnetic particles from the sample in the cuvette 8 (see FIG. 8) transferred by the container transferring section 84 of secondary reaction unit 80b. The detailed configuration of the BF separating unit 100b is the same as the BF separating unit 100a, and thus the description thereof will be omitted.

The reagent dispensing arm 90d (see FIGS. 1 and 2) has a function of dispensing the R5 reagent containing light emitting substrate in the reagent bin (not shown) arranged at the lower part of the immune analyzing device 1 into the cuvette 8 accommodating the specimen, the R1 reagent, the R2 reagent and the R3 reagent of the secondary reaction unit 80b. The reagent dispensing arm 90d includes a motor 94a, a drive transmission part 94b connected to the motor 94a, and an arm section 94d attached to the drive transmission part 94b by way of a shaft. The drive transmission part 94b is configured so as to turn the arm section 94c with the shaft as the center and move the same in the vertical direction by the driving force from the motor 94a. Furthermore, a tube 94d for discharging from the reagent bin (not shown) arranged at the lower part of the immune analyzing device 1 the R5 reagent to the cuvette 8 accommodated in the holding part 83a of the rotatable table 83.

The detecting unit 120 (see FIGS. 1 and 2) is arranged to measure the amount of antigen contained in the specimen by acquiring the light produced in the reaction process of the labeled antibody bound to the antigen of the specimen performed with the predetermined process and the light emitting substrate by means of a photo-multiplier tube. The detecting unit 120 is configured by an installing part 121 for installing the cuvette 8 accommodating the specimen, R1 reagent, R2 reagent, R3 reagent and R5 reagent, and a movement mechanism part 122 for transferring the cuvette 8 (see FIG. 8) accommodated in the holding part 83a of the rotatable table 83 of the secondary reaction unit 80b. In addition, a lid 123 is arranged in an opening and closing manner at the installing part 121 so that light does not enter from the outside into the cuvette 8 installed at the installing part 121 in time of measurement.

The disposing unit 130 (see FIGS. 1 and 2) is arranged to dispose the cuvette 8 (see FIG. 8) accommodating the measured sample measured by the detecting unit 120. The disposing unit 130 is configured by a suction part 131 (see FIG. 2) for suctioning the measured sample in the cuvette 8, and a disposing hole 132 arranged at a position spaced apart by a predetermined distance from the suction part 131. Thus, the suction part 131 suctions the measured sample, and thereafter, the used cuvette 8 is disposed into a dust box (not shown) arranged at the lower part of the immune analyzing device 1 through the disposing hole 132.

Figure 16:
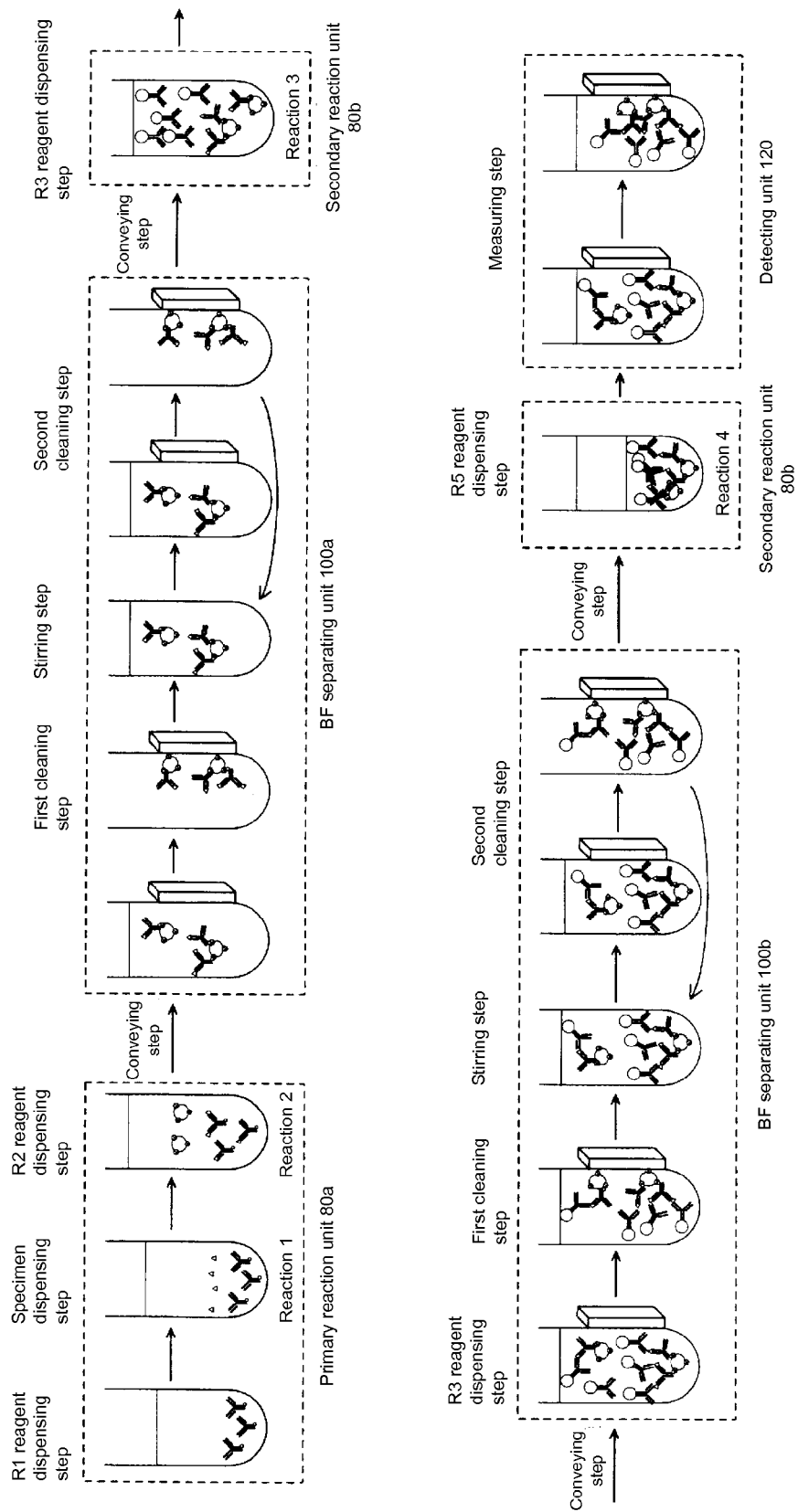
FIG. 16 is a view showing a measurement flow of the immune analyzing device according to the embodiment shown in FIG. 1.
Figure 17:
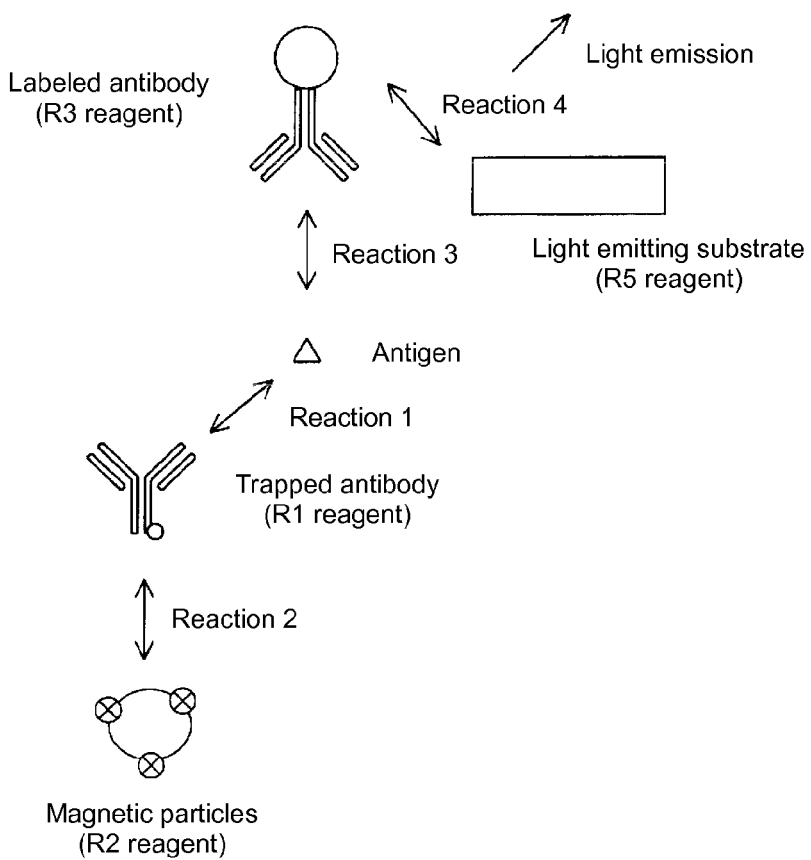
FIG. 17 is a frame format view showing the reaction between the antigen of the specimen and various reagents measured in the immune analyzing device according to the embodiment shown in FIG. 1.

FIG. 16 is a view showing the measurement flow of the immune analyzing device according to one embodiment shown in FIG. 1, and FIG. 17 is a frame format view showing the reaction between the antigen of the specimen and various reagents measured in the immune analyzing device according to one embodiment shown in FIG. 1. FIGS. 18 to 22 are views explaining the analysis operation of the immune analyzing device according to one embodiment shown in FIG. 1. The analysis operation of the immune analyzing device according to one embodiment of the present invention will now be described with reference to FIGS. 1 to 6, 8 to 11, 13, and 16 to 22.

(Cuvette Supplying Step)

First, as shown in FIGS. 1 and 2, the motor 71b of the hopper feeder 71 of the cuvette supplying unit 70 is driven, so that the cuvette 8 (see FIG. 8) is guided from the hopper 71a through the guiding plate 72 to the concave part 73b of the supporting table 73. The cuvette 8 accommodated in the concave part 73b of the supporting table 73 is transferred to the accommodating hole 81a of the rotatable table 81 of the primary reaction unit 80a by the supply catcher section 74.

(R1 Reagent Dispensing Step)

The reagent dispensing arm 90a suctions the R1 reagent in the reagent bin 5 installed in the installing part 61 of the reagent installing unit 60a, and thereafter, is rotated to the primary reaction unit 80a side, and about 150 μl of the suctioned R1 reagent is discharged to the cuvette 8 transferred by the supply catcher section 74. The R1 reagent contains trapped antibody that binds to the antigen contained in the specimen, as shown in FIGS. 16 and 17.

(Specimen Dispensing Step)

The specimen dispensing arm 50 attaches the pipette chip (see FIG. 6) conveyed to the conveying rack 23 of the emergency specimen and chip conveying unit 20 (see FIGS. 3 and 5), and thereafter, suctions specimen such as blood from the test tube 3 mounted on the rack 4 conveyed to the suction position 1a (see FIGS. 1 and 2) by the specimen conveying unit 10. The specimen dispensing arm 50 is rotated to the primary reaction unit 80a side, and discharges about 20 μl of the suctioned specimen to the cuvette 8 accommodating the R1 reagent of the accommodating hole 81a of the rotatable table 81.

(R1 Reagent and Specimen Stirring Step)

The container transferring section 82 of the primary reaction unit 80a shown in FIG. 9 stirs the cuvette 8 accommodating the R1 reagent and the specimen. Specifically, the container transferring section 82 is rotated while the specimen dispensing arm 50 is dispensing the specimen, so that the chuck portion 821c of the stirring part 821 is moved to a position facing the cuvette 8 accommodating the R1 reagent and the specimen, and thereafter, the chuck portion 821c is moved to the vicinity of the cuvette 8 towards the outer side (radial direction) from the center of the rotatable table 81. The container transferring section 82 waits until the specimen dispensing arm 50 finishes dispensing the specimen, and immediately after the dispensing of the specimen is finished, the stirring part 821 of the container transferring section 82 is further moved towards the outer side of the rotatable table 81. The cuvette 8 accommodating the R1 reagent and the specimen is thereby gripped by the chuck portion 821c of the stirring part 821. After lifting the chuck portion 821c gripping the cuvette 8 upward by driving the motor 822a of the vertical movement mechanism part 822, the motor 821f of the stirring part 821 is driven. Therefore, the R1 reagent and the specimen in the cuvette 8 are stirred when the swinging vibration of the eccentric weight 821g and the motor 821f is transmitted to the R1 reagent and the specimen in the cuvette 8 gripped by the chuck portion 821c. When the chuck portion 821c of the container transferring section 82 is moved to the vicinity of the cuvette 8 while dispensing the specimen, the cuvette 8 can be gripped by the chuck portion 821c immediately after the dispensing of the specimen is finished, the specimen and the R1 reagent in the cuvette 8 can be stirred, and the reaction between the specimen and the R1 reagent can be efficiently proceeded.

(Incubation Step (Reaction 1 Shown in FIGS. 16 and 17))

The stirred R1 reagent and specimen are incubated over a predetermined time in the cuvette 8 of the accommodating hole 81a of the rotatable table 81 rotated over a predetermined angle for every 18 seconds. Therefore, if about 162 seconds (18 seconds×9) is required for the reaction of the R1 reagent and the specimen, the cuvette 8 accommodating the R1 reagent and the specimen is rotatably transferred by nine pitches after the specimen is dispensed. The trapped antibody (R1 reagent) and the antigen of the specimen thus bind while the cuvette 8 is being rotatably transferred.

(R2 Reagent Dispensing Step)

The reagent dispensing arm 90b suctions the R2 reagent in the reagent bin 6 installed in the installing part 64 of the reagent installing unit 60b, and thereafter, is rotated to the primary reaction unit 80a side, and about 30 μl of the suctioned R2 reagent is discharged to the cuvette 8 accommodating the R1 reagent and the specimen incubated over a predetermined time. The R2 reagent contains magnetic particles that bind to the trapped antibody bound with the antigen in the specimen, as shown in FIGS. 16 and 17.

(R2 Reagent and Specimen Stirring Step)

The container transferring section 82 of the primary reaction unit 80a stirs the cuvette 8 accommodating the R1 reagent, the specimen and the R2 reagent, similar to the R1 reagent and specimen stirring step described above. That is, the chuck portion 821c of the stirring part 821 is moved to the vicinity of the cuvette 8 being dispensed with the R2 reagent while the reagent dispensing arm 90b is dispensing the R2 reagent, and the container transferring section 82 waits until the reagent dispensing arm 90b finishes dispensing the R2 reagent. Immediately after the dispensing of the R2 reagent is finished, the chuck portion 821c of the stirring part 821 of the container transferring section 82 grips the cuvette 8 accommodating the R1 reagent, the specimen and the R2 reagent, and the chuck portion 821c gripping the cuvette 8 is lifted upward, and thereafter, the motor 821f is driven to stir the R1 reagent, specimen and R2 reagent in the cuvette 8.

(Incubation Step (Reaction 2 Shown in FIGS. 16 and 17))

The stirred R1 reagent, specimen and R2 reagent are incubated over a predetermined time in the cuvette 8 of the accommodating hole 81a of the rotatable table 81. Therefore, if about 90 seconds (18 seconds×5) is required for the reaction of the trapped antibody (R1 reagent) bound to the antigen of the specimen and the magnetic particles (R2 reagent), the cuvette 8 accommodating the R1 reagent, the specimen and the R2 reagent is rotatably transferred by five pitches after the R2 reagent is dispensed. The magnetic particles (R2 reagent) and the trapped antibody (R1 reagent) bound with the antigen of the specimen thus bind while the cuvette 8 is being rotatably transferred.

(Transfer Step from Primary Reaction Unit 80a to BF Separating Unit 100a)

The cuvette 8 accommodating the incubated R1 reagent, specimen and R2 reagent is transferred to the cuvette installing hole 101d of the BF separating unit 100a shown in FIG. 11 by the container transferring section 82 of the primary reaction unit 80a. Specifically, the chuck portion 821c of the stirring part 821 is arranged so as to face the cuvette 8 rotatably transferred while being incubated by rotating the container transferring section 82, and the stirring part 821 of the container transferring section 82 is moved towards the outer side from the center of the rotatable table 81. The cuvette 8 accommodating the R1 reagent, the R2 reagent and the specimen is gripped by the chuck portion 821c of the stirring part 821. The chuck portion 821c gripping the cuvette 8 is lifted upward by driving the motor 822a of the vertical movement mechanism part 822, and the cuvette 8 is transferred to the installing part 101a of the magnetism collecting section 101 of the BF separating unit 100a by driving the motor 823a of the radial movement mechanism part 823.

The cuvette supplying step, R1 reagent dispensing step, specimen dispensing step, R1 reagent and specimen stirring step, incubation step, R2 reagent dispensing step, R2 reagent and specimen stirring step, incubation step and transfer step from primary reaction unit 80a to BF separating unit 100a in the primary reaction unit 80a are executed in parallel. The plurality of accommodating holes 81a of the rotatable table 81 are assigned with corresponding step, and the corresponding step is executed with respect to each cuvette 8 held at the accommodating hole 81a. For example, R1 reagent dispensing step is performed on the cuvette 8 held at one accommodating hole 81a, and at the same time, the specimen dispensing step is performed on the cuvette held in another accommodating hole 81a.

(First Cleaning Step in BF Separating Unit 100a)

Figure 18:
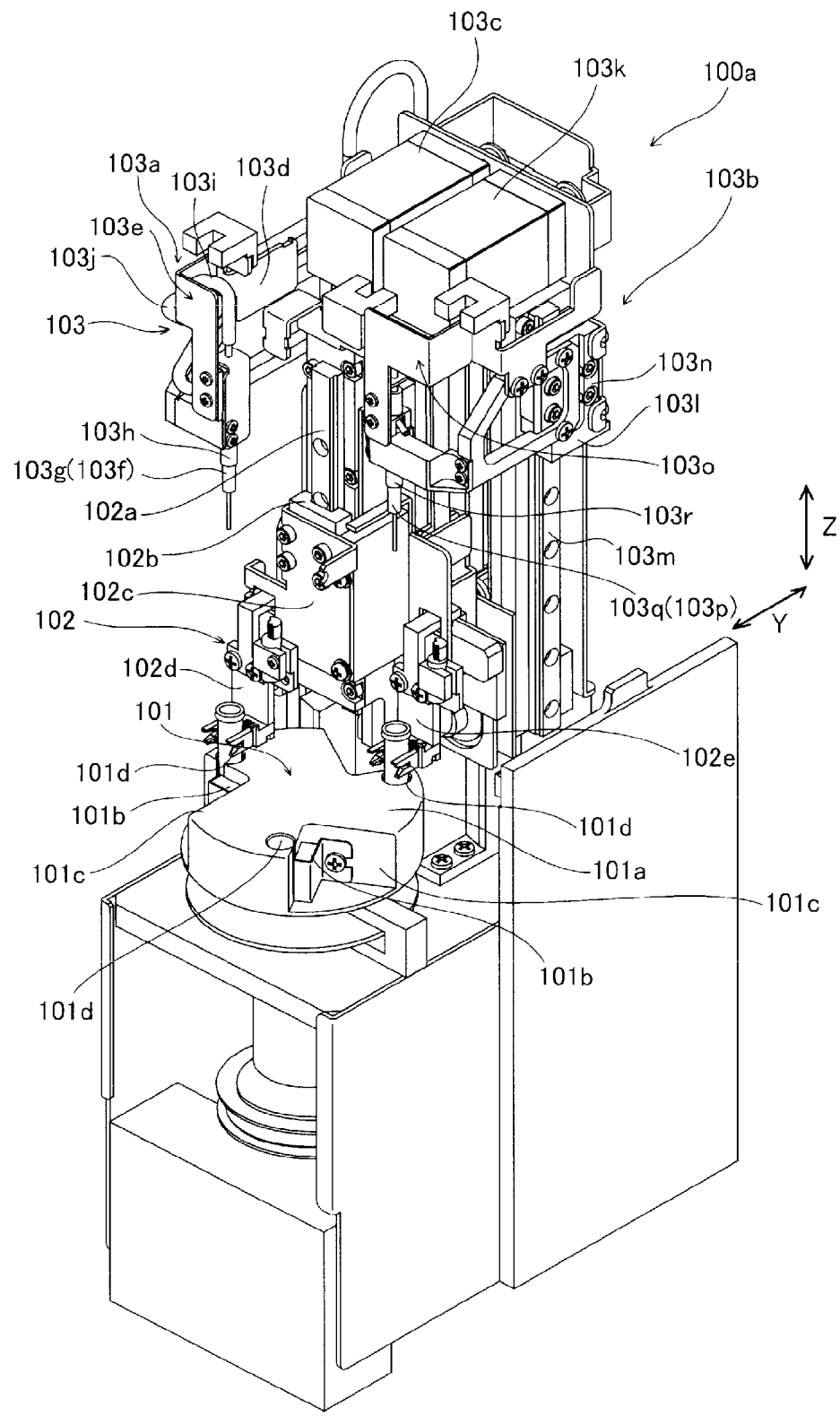
FIG. 18 is a perspective view explaining the analysis operation of the BF separating unit of the immune analyzing device according to the embodiment shown in FIG. 1.
Figure 19:
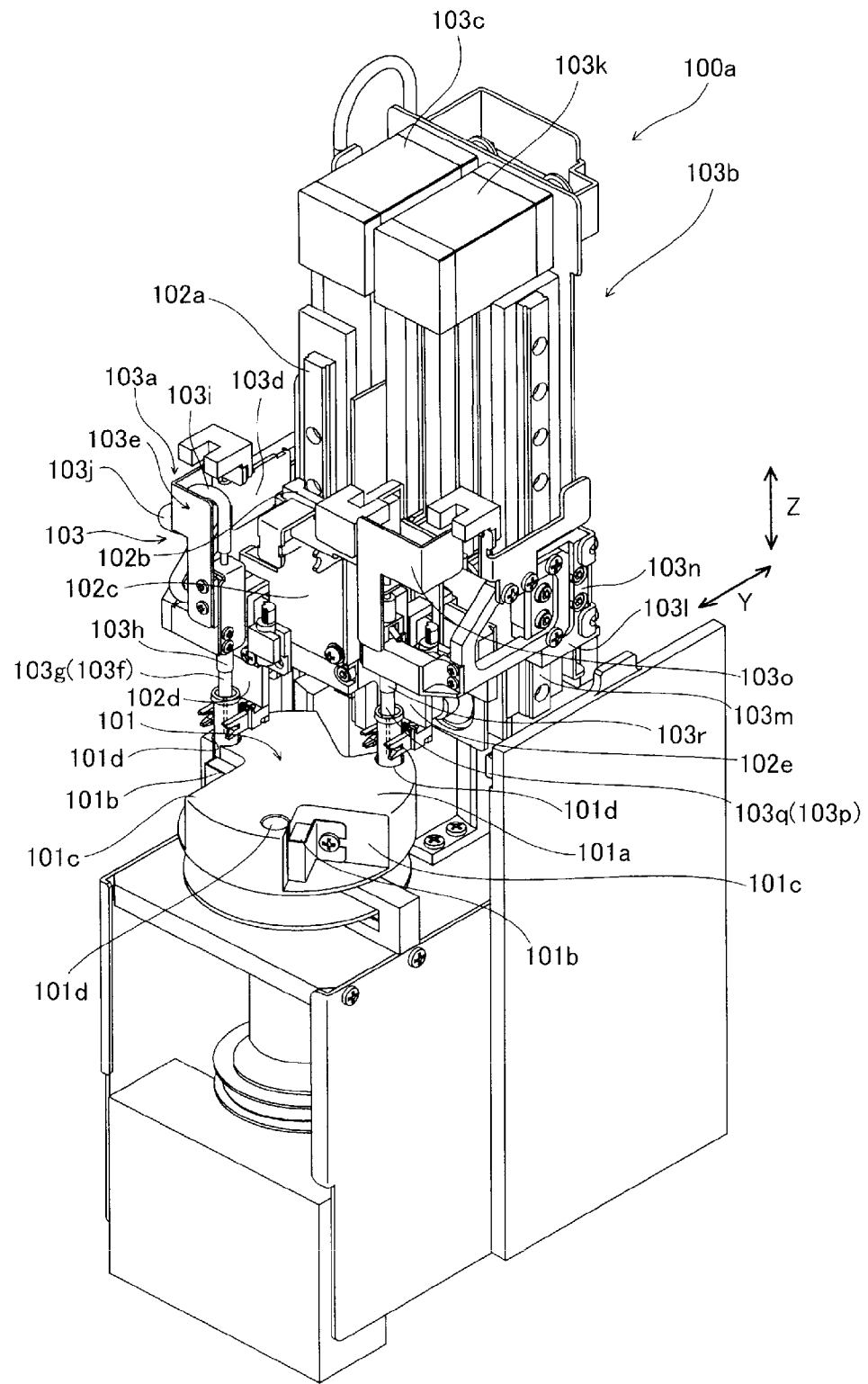
FIG. 19 is a perspective view explaining the analysis operation of the BF separating unit of the immune analyzing device according to the embodiment shown in FIG. 1.
Figure 20:
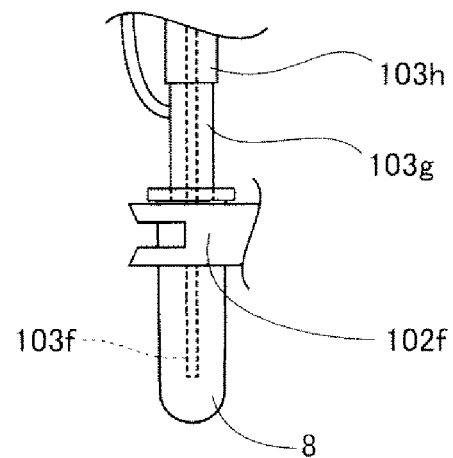
FIG. 20 is a frame format view explaining the analysis operation of the BF separating unit of the immune analyzing device according to the embodiment shown in FIG. 1.

In the present embodiment, the cuvette 8 installed in the cuvette installing hole 101d of the installing part 101a of the magnetism collecting section 101 is transferred in the rotating direction with the rotation of the installing part 101a, and is arranged at a position corresponding to the primary stirring part 102d of the stirring mechanism section 102. In this case, the magnetic particles in the cuvette 8 held at the cuvette installing hole 101d of the installing part 101a are magnetism collected by the magnet 101b arranged on the side of the cuvette 8. As shown in FIG. 18, the stirring mechanism section 102 and the separating mechanism section 103 of the BF separating unit 100a move forward (Y direction) along the common slide rail 105, and the chuck portion 102h of the primary stirring part 102d grips the cuvette 8. The nozzle portion 103f of the primary cleaning part 103e of the primary separating part 103a is inserted to the cuvette 8 in such state, as shown in FIGS. 19 and 20, and the sample in the cuvette 8 is suctioned, so that the unnecessary components excluding the magnetic particles and the antigen bound through the trapped antibody to the magnetic particles are removed. However, in the first cleaning step, some of the unnecessary components sometimes retain at the inner wall of the cuvette 8 with the magnetic particles as if caught in the magnetic particles attracted to the magnet 101b of the magnetism collecting section 101 and becomes difficult to sufficiently remove the unnecessary component, and thus the stirring step and the second cleaning step described below are performed in the present embodiment to sufficiently remove the unnecessary components.

(Stirring Step (First Time) in BF Separating Unit 100*a*)

Figure 21:
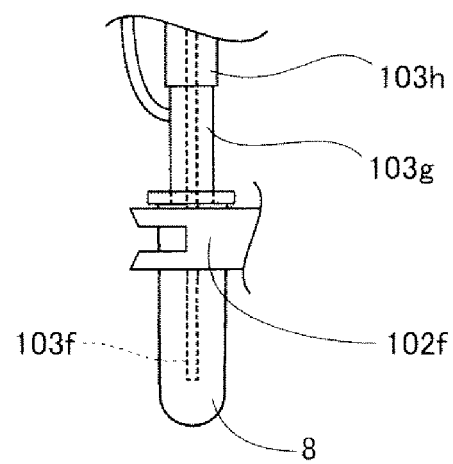
FIG. 21 is a frame format view explaining the analysis operation of the BF separating unit of the immune analyzing device according to the embodiment shown in FIG. 1.
Figure 22:
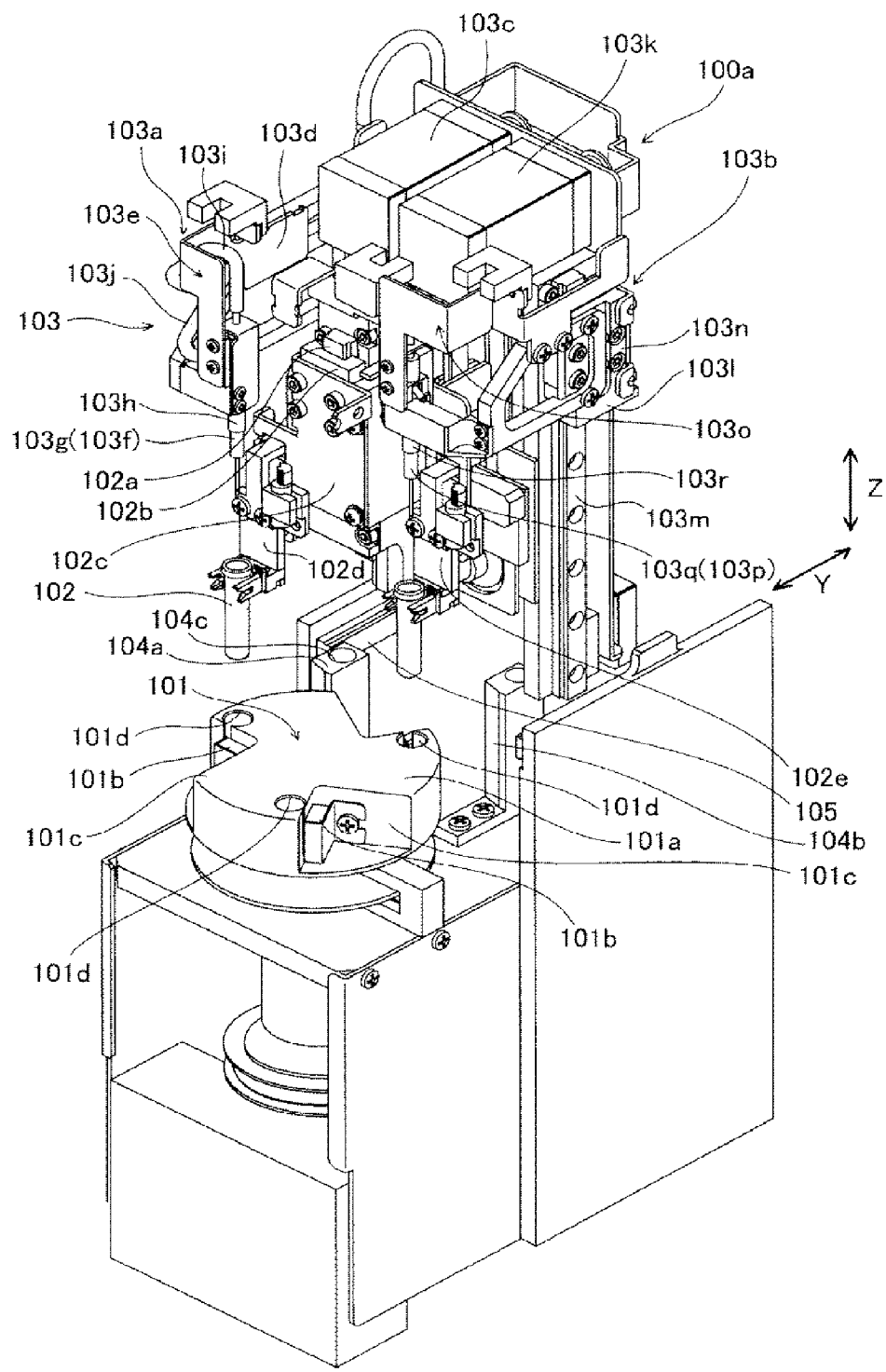
FIG. 22 is a perspective view explaining the analysis operation of the BF separating unit of the immune analyzing device according to the embodiment shown in FIG. 1.

In the present embodiment, the cleaning fluid is supplied to the cuvette 8 performed with the first cleaning step in the BF separating unit 100*a* and stirring is performed. Specifically, in the first cleaning step, immediately after suction is performed by the nozzle portion 103*f* of the primary separating part 103*a*, about 200 µl of the cleaning fluid is discharged by the supplying part 103*h* of the primary separating part 103*a*, as shown in FIG. 21. The primary stirring part 102*d* is moved upward (Z direction) along the slide rail 102*a* from the state in which the chuck portion 102*h* of the primary stirring part 102*d* is gripping the cuvette 8. As shown in FIGS. 13 and 22, when the motor 102*j* is driven with the cuvette 8 in the lifted state, the swinging vibration of the eccentric weight 102*k* and the motor 102*j* is transmitted to the cuvette 8 gripped at the chuck portion 102*h*, and the cleaning fluid, the unnecessary component and the magnetic particles in the cuvette 8 are stirred. The unnecessary components are then caught in the magnetic particles and the unnecessary components retained at the inner wall of the cuvette 8 are dispersed with the magnetic particles.

(Second Cleaning Step (First Time) in BF Separating Unit 100*a*)

In the present embodiment, the cuvette 8 stirred in the BF separating unit 100*a* is again held in the cuvette installing hole 101*d* of the magnetism collecting section 101, as shown in FIG. 18, and the magnetic particles are collected on the magnet 101*b* side arranged on the side of the cuvette 8. After the magnetic particles in the cuvette 8 are collected, the cleaning fluid and the unnecessary component are discharged, as shown in FIGS. 19 and 20. That is, after the nozzle portion 103*f* of the primary cleaning part 103*e* of the primary separating part 103*a* is inserted into the cuvette 8, the cleaning fluid in the cuvette 8 is suctioned, so that the unnecessary components remaining by being caught in the magnetic particles are removed.

(Stirring Step (Second Time) in BF Separating Unit 100*a*)

In the present embodiment, the cleaning fluid is supplied to the cuvette 8 performed with the second cleaning step of the first time in the BF separating unit 100*a* and stirring is performed. Specifically, as shown in FIG. 21, immediately after suction of the cleaning fluid and the unnecessary components is performed by the nozzle portion 103*f* of the primary separating part 103*a* in the second cleaning step of the first time, about 200 µl of the cleaning fluid is discharged by the supplying part 103*h* of the primary separating part 103*a*. The cleaning fluid, the slightly remaining unnecessary components, and the magnetic particles and R1 reagent in the cuvette 8 are stirred, as shown in FIGS. 13 and 22 with the chuck portion 102*h* of the primary stirring part 102*d* lifting the cuvette 8 upward.

(Second Cleaning Step (Second Time) in BF Separating Unit 100*a*)

In the present embodiment, the cuvette 8 stirred in the BF separating unit 100*a* is again held in the cuvette installing hole 101*d* of the magnetism collecting section 101, and the magnetic particles are collected on the magnet 101*b* side arranged on the side of the cuvette 8, as shown in FIG. 18. After the magnetic particles in the cuvette 8 are collected, the cleaning fluid and the slightly remaining unnecessary component are reliably discharged, as shown in FIGS. 19 and 20. That is, after the nozzle portion 103*f* of the primary cleaning part 103*e* of the primary separating part 103*a* is inserted into the cuvette 8, the cleaning fluid in the cuvette 8 is suctioned, so that the slightly remaining unnecessary components are reliably removed. Immediately after the cleaning fluid and the unnecessary components are suctioned, about 200 µl of the cleaning fluid is discharged by the supplying part 103*h* of the primary separating part 103*a*, as shown in FIG. 21. Thereafter, the cuvette 8 accommodating the cleaning fluid and the magnetic particles is transferred in the rotating direction by 120 degrees with the rotation over 120 degrees of the installing part 101*a* while being magnetism collected by the magnet 101*b* of the magnetism collecting section 101, and arranged at a position corresponding to the secondary stirring part 102*e* of the stirring mechanism section 102. The nozzle portion 103*f* of the primary separating part 103*a* is cleaned by discharging the cleaning fluid while being inserted to the hole 104*c* of the nozzle cleaning section 104*a* (see FIG. 11) for each time the sample in the cuvette 8 is suctioned, as shown in FIG. 16.

(Stirring Step (Third Time) in BF Separating Unit 100*a*)

Similar to the stirring step (first time and second time) performed by the primary stirring part 102*d* of the BF separating unit 100*a*, the cuvette 8 accommodating about 200 µl of cleaning fluid supplied by the supplying part 103*h* of the primary separating part 103*a* is stirred by the secondary stirring part 102*e* of the BF separating unit 100*a*, as shown in FIGS. 13 and 22.

(Second Cleaning Step (Third Time) in BF Separating Unit 100*a*)

Similar to the second cleaning step (first time and second time) performed by the primary separating part 103*a* of the BF separating unit 100*a*, the cleaning fluid in the cuvette 8 is suctioned by the secondary separating part 103*b* of the BF separating unit 100*a*, as shown in FIGS. 19 and 20.

(Stirring Step (Fourth Time) in BF Separating Unit 100*a*)

Furthermore, similar to the stirring step (third time) performed by the secondary separating part 103*b* of the BF separating unit 100*a*, the cuvette 8 accommodating about 200 µl of cleaning fluid supplied by the supplying part 103*r* of the secondary separating part 103*b* is stirred by the supplying part 103*r* of the secondary separating part 103*b*.

(Second Cleaning Step (Fourth Time) in BF Separating Unit 100*a*)

Similar to the second cleaning step (third time) performed by the secondary separating part 103*b* of the BF separating unit 100*a*, the cleaning fluid in the cuvette 8 is suctioned by the secondary separating part 103*b* of the BF separating unit 100*a*. Thereafter, the cuvette 8 accommodating the sample removed with the unnecessary components and having the magnetic particles of solid phase as the main components is transferred in the rotating direction with the rotation of the installing part 101*a* of the BF separating unit 100*a*, as shown in FIGS. 1 and 2, and transferred to a position of being gripped by the chuck portion 110*g* of the movement catcher unit 110. The nozzle portion 103*p* of the secondary separating part 103*b* is cleaned by discharging the cleaning fluid while being inserted to the hole of the nozzle cleaning section 104*b* (see FIG. 11) each time the sample in the cuvette 8 is suctioned.

(Transfer Step from BF Separating Unit 100*a* to Secondary Reaction Unit 80*b*)

The cuvette 8 performed with separation of unnecessary components and magnetic particles by the BF separating unit 100*a* is gripped by the chuck portion 110*g* of the movement catcher unit 110 and transferred to the holding part 83*a* of the rotatable table 83 of the secondary reaction unit 80*b*, as shown in FIGS. 1 and 2.

(R3 Reagent Dispensing Step)

The reagent dispensing arm 90c suctions the R3 reagent in the reagent bin 7 installed in the installing part 61 of the reagent installing part 60a, and thereafter, rotated to the secondary reaction unit 80b side, and discharges about 100 μl of the R3 reagent suctioned to the cuvette 8 accommodating the magnetic particles (R2 reagent) and the antigen of the specimen bound through the trapped antibody (R1 reagent). The R3 reagent contains labeled antibody that binds to the antigen in the specimen, as shown in FIGS. 16 and 17.

(R3 Reagent and Specimen Stirring Step)

The container transferring section 84 of the secondary reaction unit 80b stirs the cuvette 8 accommodating the trapped antibody (R1 reagent), the antigen (specimen), the magnetic particles (R2 reagent) and the R3 reagent containing the labeled antibody, similar to the stirring step of the R1 reagent and the specimen described above.

(Incubation Step (Reaction 3 Shown in FIGS. 16 and 17))

The stirred trapped antibody (R1 reagent), antigen (specimen), magnetic particles (R2 reagent), and the R3 reagent containing labeled antibody are incubated over a predetermined time in the cuvette 8 of the holding part 83a of the rotatable table 83. Therefore, if about 198 seconds (18 seconds x 11) is required for the reaction of the antigen of the specimen and the labeled antibody (R3 reagent), the cuvette 8 accommodating the trapped antibody (R1 reagent), antigen (specimen), magnetic particles (R2 reagent), and the R3 reagent containing labeled antibody is rotatably transferred by eleven pitches after the R3 reagent is dispensed. The antigen bound with the magnetic particles (R2 reagent) through the trapped antibody (R1 reagent) and the labeled antibody (R3 reagent) bound while the cuvette 8 is being rotatably transferred.

(Transfer Step from Secondary Reaction Unit 80b to BF Separating Unit 100b)

The cuvette 8 accommodating the incubated trapped antibody (R1 reagent), antigen (specimen), magnetic particles (R2 reagent), and R3 reagent containing labeled antibody is transferred to the cuvette installing hole 101d of the BF separating unit 100b by the container transferring section 84 of the secondary reaction unit 80b, similar to the transfer step from the primary reaction unit 80a to the BF separating unit 100a described above.

(First Cleaning Step, Stirring Step, and Second Cleaning Step in BF Separating Unit 100b)

In the present embodiment, the first cleaning step, four stirring steps and the second cleaning step are performed in the BF separating unit 100b, similar to the first cleaning step, four stirring steps and the second cleaning step in the BF separating unit 100a described above. Thus, the R3 reagent (unnecessary component) containing the labeled antibody that does not bind with the antigen of the specimen can be sufficiently removed. The cuvette 8 accommodating the sample including the antigen bound with the labeled antibody removed with the unnecessary components is thereafter transferred in the rotating direction with the rotation of the magnetism collecting section of the BF separating unit 100b, and transferred to a position movable by the container transferring section 84 of the secondary reaction unit 80b.

(Transfer Step from BF Separating Unit 100a to Secondary Reaction Unit 80b)

The cuvette 8 separated with the unnecessary components and the magnetic particles by the BF separating unit 100b is again transferred to the holding part 83a of the rotatable table 83 by the container transferring section 84 of the secondary reaction unit 80b, as shown in FIGS. 1 and 2.

(R5 Reagent Dispensing Step)

The reagent dispensing arm 90d discharges only about 100 μl of the R5 reagent containing light emitting substrate in the reagent bin (not shown) arranged at the lower part of the immune analyzing device 1 to the cuvette 8 accommodating the trapped antibody (R1 reagent), the magnetic particles (R2 reagent), the labeled antibody (R3 reagent) and the antigen of the specimen through the tube 94d. The light emitting substrate that reacts with the labeled antibody of the R3 reagent and emits light is contained in the R5 reagent, as shown in FIGS. 16 and 17.

(R5 Reagent and Labeled Antibody Stirring Step)

The container transferring section 84 of the secondary reaction unit 80b stirs the cuvette 8 accommodating the trapped antibody (R1 reagent), the antigen (specimen), the magnetic particles (R2 reagent), the labeled antibody (R3 reagent) and the R5 reagent containing the light emitting substrate, similar to the R1 reagent and the specimen stirring step described above.

(Incubation Step (Reaction 4 Shown in FIGS. 16 and 17))

The stirred trapped antibody (R1 reagent), antigen (specimen), magnetic particles (R2 reagent), and labeled antibody (R3 reagent) and R5 reagent containing light emitting substrate are incubated over a predetermined time in the cuvette 8 of the holding part 83a of the rotatable table 83. Therefore, if about 378 seconds (18 seconds×21) is required for the reaction of the labeled (R3 reagent) bound to the antigen of the specimen and the R5 reagent containing light emitting substrate, the cuvette 8 accommodating the trapped antibody (R1 reagent), antigen (specimen), magnetic particles (R2 reagent), and labeled antibody (R3 reagent) and R5 reagent containing light emitting substrate is rotatably transferred by 21 pitches after the R5 reagent is dispensed. The reaction between the labeled antibody (R3 reagent) and the light emitting substrate (R5 reagent) proceeds while the cuvette 8 is being rotatably transferred.

Similar to the primary reaction unit 81a, the transfer step from the BF separating unit 100a to the secondary reaction unit 80b, the R3 reagent dispensing step, the R3 reagent and specimen stirring step, the incubation step, the transfer step from secondary reaction unit 80b to BF separating unit 100b, the transfer step from BF separating unit 100b to secondary reaction unit 80b, the R5 reagent dispensing step, the R5 reagent and labeled antibody stirring step, and the incubation step in the secondary reaction unit 80b described above are performed in parallel.

(Measuring Step)

Subsequently, the cuvette 8 accommodating the incubated trapped antibody (R1 reagent), the antigen (specimen), the magnetic particles (R2 reagent), the labeled antibody (R3 reagent) and the R5 reagent containing the light emitting substrate is conveyed to the installing part 121 by the conveying mechanism section 122 of the detecting unit 120, as shown in FIGS. 1 and 2. In time of measurement, the lid 123 is closed so that the inside of the installing part 121 is shielded from external light, and measurement is performed under the condition the external light is shielded. The magnetic particles in the cuvette 8 installed in the installing part 121 are attracted to the magnet side, as shown in FIG. 16. Thus, the measurement of the light emitting amount is suppressed from being inhibited magnetic particles when measuring the light emitting amount generated in the reaction process of the labeled antibody of the R3 reagent and the light emitting substrate of the R5 reagent. The light emitting amount generated in the reaction process of the labeled antibody of R3 reagent and the light emitting substrate of the R5 reagent is acquired in the photo-multiplier tube (not shown) under such condition.

(Disposing Step)

As shown in FIGS. 1 and 2, the cuvette 8 accommodating the measured sample performed with the measurement is conveyed to the position below the suction part 131 (see FIG. 2) of the disposing unit 130 by the conveying mechanism section 122 of the detecting unit 120. The suction part 131 of the disposing unit 130 moves downward, suctions the measured sample, and empties the cuvette 8. Thereafter, the conveying mechanism part 122 of the detecting unit 120 gripping the empty cuvette 8 is rotated so as to be conveyed to the position corresponding to the disposing hole 132 of the disposing unit 130, and thereafter, the empty cuvette 8 is dropped into the disposing hole 132, and the used cuvette 8 is disposed into the dust box (not shown) arranged at the lower part of the immune analyzing device 1 through the discarding hole 132. The analysis operation of the immune analyzing device 1 according to the present embodiment is performed in the above manner In the present embodiment, since the container transferring section 82 (container transferring section 84) is arranged on the upper part of the rotatable table 81 (rotatable table 83) as described above, the movement amount of the container transferring section 82 (container transferring section 84) does not vary, and the cuvette 8 accommodated in the accommodating hole of any position can be easily held even when holding the cuvette 8 accommodated in any accommodating hole of the rotatable table 81 (rotatable table 83). Therefore, even when transferring the cuvette 8 at a plurality of positions of the rotatable table 81 (rotatable table 83), a plurality of container transferring sections do not need to be arranged, whereby miniaturization of the device and reduction of cost are achieved. Furthermore, even when holding the cuvette 8 accommodated in the accommodating hole of any position, the movement amount of the container transferring section 82 (container transferring section 84) does not vary, and the movement amount of the container transferring section 82 (container transferring section 84) is suppressed. Moreover, since the cuvette 8 accommodated in the accommodating hole of any position can be easily held, various specimen processing sequences can be flexibly responded.

In the present embodiment, the plurality of accommodating holes are arranged in circular ring shape, and the container transferring section 82 (container transferring section 84) is preferably arranged at substantially the center of circular ring formed by a plurality of accommodating holes. Thus, the distance between the container transferring section 82 (container transferring section 84) and all the cuvettes 8 accommodated in the accommodated hole become substantially the same. Therefore, the movement amount of the container transferring section 82 (container transferring section 84) become substantially constant regardless of at which accommodating hole of the rotatable table 81 (rotatable table 83) the cuvette 8 is accommodated, and thus the cuvette 8 accommodated in the accommodating hole of any position can be more easily held, and various specimen processing sequences can be more flexibly responded.

In the present embodiment, the container transferring section 82 (container transferring section 84) is preferably configured so as to transfer the cuvette 8 in the vertical direction, the rotating direction of the rotatable table 81 (rotatable table 83) and the radial direction of the circular ring formed by a plurality of accommodating holes. Thus, the container transferring section 82 (container transferring section 84) transfers the holding cuvette 8 in the rotating direction to the position facing the target accommodating hole and thereafter, transfers the same in the radial direction until reaching the target accommodating hole even when transferring the cuvette 8 to the accommodating hole of any position, whereby the cuvette 8 can be efficiently transferred by the operation adapted to the arrangement of the accommodating hole.

In the present embodiment, the stirring part 821 is preferably configured so as to be able to stir the specimen and the reagent in the cuvette 8 while holding the cuvette 8. Thus, the mixed liquid of the specimen and the reagent is stirred with the container transferring section 82 (container transferring section 84) holding the cuvette 8, whereby the mixed solution can be rapidly stirred.

In the present embodiment, the stirring part 821 is preferably configured so as to move to the vicinity of the cuvette to be dispensed with reagent when the reagent dispensing arms 90a, 90b, 90c and 90d dispense the reagents into the cuvette. Reaction occurs after the specimen and the reagent are mixed, but such reaction proceeds efficiently by sufficiently stirring the specimen and the reagent. Therefore, according to the above configuration, after the specimen or the reagent is dispensed into the cuvette 8, the specimen and the reagent are rapidly stirred, and the reaction of the specimen and the reagent is efficiently proceeds.

In the present embodiment, by arranging the stirring mechanism section 102 for stirring the sample in the cuvette 8 and the magnetism collecting section 101 for holding the cuvette 8 and collecting the magnetic particles (R2 reagent) in the cuvette 8 in the BF separating unit 100a, when the sample in the cuvette 8 is stirred by the primary stirring part 102d of the stirring mechanism section 102 in the BF separating unit 100a, the magnetic particles and the unnecessary components integrated with the magnetic particles by being caught thereto are dispersed, and the unnecessary components are removed with the magnetic particles in the sample in which the magnetic particles and the unnecessary components are dispersed by the magnetism collecting section 101 attracted to the magnet 101b side, whereby the unnecessary components caught in the magnetic particles can be removed. Consequently, the unnecessary components not necessary for the analysis of the immune analyzing device 1 are sufficiently removed.

In the present embodiment, by arranging the separating mechanism section 103 for discharging the unnecessary components after supplying the cleaning fluid to the cuvette 8 in the BF separating unit 100a in addition to the magnetism collecting section 101 and the stirring mechanism section 102, the cleaning fluid for dispersing the integrated magnetic particles and the unnecessary components caught in the magnetic particles is easily supplied by the supplying part 103h of the separating mechanism section 103 in the BF separating unit 100a, and the unnecessary components in the cuvette 8 held at the magnetism collecting section 101 are easily discharged. As a result, a series of process for removing the unnecessary components are performed in the BF separating unit 100a, and thus the process of removing the unnecessary components is more rapidly performed.

In the present embodiment, the BF separating unit 100a and the BF separating unit 100b are individually arranged, so that when performing the removal of the unnecessary components after dispensing the R2 reagent and the removal of the unnecessary components after dispensing the R3 reagent, the removal of the unnecessary components for the first time after dispensing the R2 reagent is performed in the BF separating unit 100a and the removal of the unnecessary components for the second time after dispensing the R3 reagent is performed in the BF separating unit 100b. As a result, the removal of the unnecessary components for the second time is performed in the BF separating unit 100b while the removal of the unnecessary components for the first time is performed in the BF separating unit 100a, and thus the process of removing the unnecessary components is rapidly performed compared to when the removal of the unnecessary components for the first time and the second time is performed in one BF separating unit.

In the present embodiment, three cuvette installing holes 101d are arranged in the magnetism collecting section 101 of the BF separating unit 100a, and two stirring parts (primary stirring part 102d and secondary stirring part 102e) and two cleaning parts (primary cleaning part 103e and secondary cleaning part 103o) are arranged in the stirring mechanism section 102 of the BF separating unit 100a, so that three transferred cuvettes 8 can be accommodated in the cuvette installing holes 101d of the magnetism collecting section 101. Therefore, the sample in the cuvette 8 accommodated in one cuvette installing hole 101d can be stirred by the primary stirring part 102d and the unnecessary components can be removed by the primary cleaning part 103e, while the sample in the cuvette 8 accommodated in another cuvette installing hole 101d is stirred by the secondary stirring part 102e and the unnecessary components are removed by the secondary cleaning part 103o. As a result, the samples in the two cuvettes 8 can be simultaneously processed in one BF separating unit 100a, which further enhances the processing ability in the BF separating unit 100a.

In the present embodiment, the installing part 101a including three cuvette installing holes 101d is rotatably configured, so that after processing the sample in the cuvette 8 by the primary stirring part 102d and the primary cleaning part 103e with the cuvette installing hole 101d holding the cuvette 8 transferred by the container transferring section 82 moved to a position corresponding to the primary stirring part 102d and the primary cleaning part 103e, the installing part 101a is rotated to move the cuvette installing hole 101d holding the cuvette 8 to the position corresponding to the secondary stirring part 102e. Therefore, the sample in the cuvette 8 processed by the primary stirring part 102d and the primary cleaning part 103e can again be processed by the secondary stirring part 102e and the secondary cleaning part 103o. That is, the second cleaning step of the first and second times is performed in the primary stirring part 102d and the primary cleaning part 103e while the second cleaning step of the third and fourth time is performed in the secondary stirring part 102e and the secondary cleaning part 103o. As a result, the second cleaning step of a plurality of times (four times in the present embodiment) are performed in parallel in one BF separating unit 100a, whereby the lowering of the processing ability in the BF separating unit 100a is suppressed even if the removal of unnecessary components is performed over a plurality of times to sufficiently clean the unnecessary components.

In the present embodiment, the stirring mechanism section 102 for stirring the sample in the cuvette 8 is arranged in the BF separating unit 100a for separating the magnetic particles and the unnecessary components from the sample in the cuvette 8 conveyed by the container conveying unit 82 as described above, whereby the sample in the cuvette 8 is stirred in the BF separating unit 100a. Therefore, the cuvette does not need to be conveyed to another device including the stirring part to disperse the integrated magnetic particles and the unnecessary components caught in the magnetic particles, whereby the process of removing the unnecessary components is rapidly performed compared to when conveying the cuvette 8 to another device and stirring and then returning the cuvette to the BF separating unit 100a. As a result, the processing ability of removing the unnecessary components in the BF separating unit 100a enhances.

In the present embodiment, by arranging the stirring mechanism section 102 for stirring the sample in the cuvette 8 and the magnetism collecting section 101 for holding the cuvette 8 and collecting the magnetic particles (R2 reagent) in the cuvette 8 in the BF separating unit 100a, when the sample in the cuvette 8 is stirred by the primary stirring part 102d of the stirring mechanism section 102 in the BF separating unit 100a, the magnetic particles and the unnecessary components integrated with the magnetic particles by being caught thereto are dispersed, and the unnecessary components are removed with the magnetic particles in the sample in which the magnetic particles and the unnecessary components are dispersed by the magnetism collecting section 101 attracted to the magnet 101b side, whereby the unnecessary components caught in the magnetic particles can be removed. Consequently, the unnecessary components not necessary for the analysis of the immune analyzing device 1 are sufficiently removed.

In the present embodiment, by arranging the separating mechanism section 103 for discharging the unnecessary components after supplying the cleaning fluid to the cuvette 8 in the BF separating unit 100a in addition to the magnetism collecting section 101 and the stirring mechanism section 102, the cleaning fluid for dispersing the integrated magnetic particles and the unnecessary components caught in the magnetic particles is easily supplied by the supplying part 103h of the separating mechanism section 103 in the BF separating unit 100a, and the unnecessary components in the cuvette 8 held at the magnetism collecting section 101 are easily discharged. As a result, a series of process for removing the unnecessary components are performed in the BF separating unit 100a, and thus the process of removing the unnecessary components is more rapidly performed.

In the present embodiment, the BF separating unit 100a and the BF separating unit 100b are individually arranged, so that when performing the removal of the unnecessary components after dispensing the R2 reagent and the removal of the unnecessary components after dispensing the R3 reagent, the removal of the unnecessary components for the first time after dispensing the R2 reagent is performed in the BF separating unit 100a and the removal of the unnecessary components for the second time after dispensing the R3 reagent is performed in the BF separating unit 100b. As a result, the removal of the unnecessary components for the second time is performed in the BF separating unit 100b while the removal of the unnecessary components for the first time is performed in the BF separating unit 100a, and thus the process of removing the unnecessary components is rapidly performed compared to when the removal of the unnecessary components for the first time and the second time is performed in one BF separating unit.

In the present embodiment, three cuvette installing holes 101d are arranged in the magnetism collecting section 101 of the BF separating unit 100a, and two stirring parts (primary stirring part 102d and secondary stirring part 102e) and two cleaning parts (primary cleaning part 103e and secondary cleaning part 103o) are arranged in the stirring mechanism section 102 of the BF separating unit 100a, so that three transferred cuvettes 8 can be accommodated in the cuvette installing holes 101d of the magnetism collecting section 101. Therefore, the sample in the cuvette 8 accommodated in one cuvette installing hole 101d can be stirred by the primary stirring part 102d and the unnecessary components can be removed by the primary cleaning part 103e, while the sample in the cuvette 8 accommodated in another cuvette installing hole 101d is stirred by the secondary stirring part 102e and the unnecessary components are removed by the secondary cleaning part 103o. As a result, the samples in the two cuvettes 8 can be simultaneously processed in one BF separating unit 100a, which further enhances the processing ability in the BF separating unit 100a.

In the present embodiment, the installing part 101a including three cuvette installing holes 101d is rotatably configured, so that after processing the sample in the cuvette 8 by the primary stirring part 102d and the primary cleaning part 103e with the cuvette installing hole 101d holding the cuvette 8 transferred by the container transferring section 82 moved to a position corresponding to the primary stirring part 102d and the primary cleaning part 103e, the installing part 101a is rotated to move the cuvette installing hole 101d holding the cuvette 8 to the position corresponding to the secondary stirring part 102e. Therefore, the sample in the cuvette 8 processed by the primary stirring part 102d and the primary cleaning part 103e can again be processed by the secondary stirring part 102e and the secondary cleaning part 103o. That is, the second cleaning step of the first and second times is performed in the primary stirring part 102d and the primary cleaning part 103e while the second cleaning step of the third and fourth time is performed in the secondary stirring part 102e and the secondary cleaning part 103o. As a result, the second cleaning step of a plurality of times (four times in the present embodiment) are performed in parallel in one BF separating unit 100a, whereby the lowering of the processing ability in the BF separating unit 100a is suppressed even if the removal of unnecessary components is performed over a plurality of times to sufficiently clean the unnecessary components.

The embodiments disclosed herein should be recognized as merely illustrative and should not be recognized as being exclusive in any way. The scope of the present invention is defined by the appended claims rather than by the description preceding them, and all changes that fall within meets and bounds of the claims, or equivalence of such meets and bounds are therefore intended to be embraced by the claims.

For example, a case of arranging two BF separating units has been described in the above embodiment, but the present invention is not limited thereto, and the magnetic particles and the unnecessary components may be separated by one BF separating unit or the magnetic particles and the unnecessary components may be separated by three or more BF separating units. In the present embodiment, the unnecessary components and the magnetic particles are separated by the BF separating unit 100a after dispensing the R2 reagent, and then the unnecessary components and the magnetic particles are separated by the BF separating unit 100b after dispensing the R3 reagent, but the unnecessary components and the magnetic particles may be separated by the BF separating unit 100b only after dispensing the R3 reagent without separating the unnecessary components and the magnetic particles after dispensing the R2 reagent depending on the measurement items.

An example of performing a first cleaning step and a second cleaning step in the BF separating unit has been described in the above embodiment, but the present invention is not limited thereto, and the cleaning step of filling the cuvette with cleaning fluid and then discharging the cleaning fluid may be performed with the magnetic particles in the cuvette collected separate from the first cleaning step and the second cleaning step. The sample scattered and attached to the inner wall surface side of the upper part of the cuvette are thereby suppressed from drying and retaining at the relevant position. As a result, analysis is performed including the sample scattered and attached to the inner wall surface side of the upper part of the cuvette, whereby accurate analysis is performed.

An example of arranging three cuvette installing holes in the BF separating unit and arranging three magnets on the side of the cuvette accommodated in the cuvette installing hole has been described in the above embodiment, but the present invention is not limited thereto, and two or less cuvette installing holes and magnets may be arranged or four or more cuvette installing holes and magnets may be arranged.

An example of arranging two stirring part (primary stirring part and secondary stirring part) and two cleaning part (primary cleaning part and secondary cleaning part) in the BF separating unit has been described in the above embodiment, but the present invention is not limited thereto, and one stirring part and one cleaning part may be arranged in the BF separating unit or three or more stirring parts and cleaning parts may be arranged in the BF separating unit.

An example of stirring the sample in the cuvette by the stirring part of the BF separating unit when performing the BF separating process has been described in the above embodiment, but the present invention is not limited thereto, and the sample in the cuvette may be stirred by the stirring part of the container transferring section.

For example, a case of arranging two BF separating units has been described in the above embodiment, but the present invention is not limited thereto, and the magnetic particles and the unnecessary components may be separated by one BF separating unit or the magnetic particles and the unnecessary components may be separated by three or more BF separating units. In the present embodiment, the unnecessary components and the magnetic particles are separated by the BF separating unit 100a after dispensing the R2 reagent, and then the unnecessary components and the magnetic particles are separated by the BF separating unit 100b after dispensing the R3 reagent, but the unnecessary components and the magnetic particles may be separated by the BF separating unit 100b only after dispensing the R3 reagent without separating the unnecessary components and the magnetic particles after dispensing the R2 reagent depending on the measurement items.

An example of performing a first cleaning step and a second cleaning step in the BF separating unit has been described in the above embodiment, but the present invention is not limited thereto, and the cleaning step of filling the cuvette with cleaning fluid and then discharging the cleaning fluid may be performed with the magnetic particles in the cuvette collected separate from the first cleaning step and the second cleaning step. The sample scattered and attached to the inner wall surface side of the upper part of the cuvette are thereby suppressed from drying and retaining at the relevant position. As a result, analysis is performed including the sample scattered and attached to the inner wall surface side of the upper part of the cuvette, whereby accurate analysis is performed.

An example of arranging three cuvette installing holes in the BF separating unit and arranging three magnets on the side of the cuvette accommodated in the cuvette installing hole has been described in the above embodiment, but the present invention is not limited thereto, and two or less cuvette installing holes and magnets may be arranged or four or more cuvette installing holes and magnets may be arranged.

An example of arranging two stirring part (primary stirring part and secondary stirring part) and two cleaning part (primary cleaning part and secondary cleaning part) in the BF separating unit has been described in the above embodiment, but the present invention is not limited thereto, and one stirring part and one cleaning part may be arranged in the BF separating unit or three or more stirring parts and cleaning parts may be arranged in the BF separating unit.

An example of stirring the sample in the cuvette by the stirring part of the BF separating unit when performing the BF separating process has been described in the above embodiment, but the present invention is not limited thereto, and the sample in the cuvette may be stirred by the stirring part of the container transferring section.

What is claimed is:

1. A separation processing device used in an analyzer for measuring a target substance in a biological sample, comprising:
    an installing device having a plurality of installing holes for holding a respective reaction container containing a reacted sample prepared by reacting a target substance contained in a biological sample and magnetic particles for capturing the target substance;
    a corresponding magnet which is embedded within the installing device in close proximity adjacent to a side of each of the installing hole;
    a discharging tube including a suction nozzle which has a suction port at a lower end;
    a supplying device including a supply port having a tube connecting the supply port to a tank which stores a washing liquid;
    a stirring mechanism device including:
        a slide rail extending in a vertical z direction,
        a movement member which moves in the vertical z direction along the slide rail, and
        a stirring member which is attached to the movement member and includes a chuck portion configured to grip the reaction container, a motor and an eccentric weight attached to a shaft of the motor; and
    a controller configured to control the separation processing device,
        wherein the controller configures the separation processing device to perform steps in sequence, comprising:
        prior to stirring the reaction container, collecting magnetic particles in the reaction container held in the installing hole by the magnet;
        removing a residue other than the magnetic particles by the discharging tube while the magnet collects the magnetic particles which are left behind in the reaction container;
        supplying by the supplying device, the washing liquid into the reaction container from which the residue has been removed;
        raising by the movement member, the reaction container which contains the washing liquid and is gripped by the chuck portion along the slide rail to a stir position above the installing hole of the installing device;
        afterwards, stirring the left behind magnetic particles and the washing liquid in the reaction container which is out of the installing hole and is gripped by the chuck portion at the stir position using the motor and the eccentric weight;
        lowering by the movement member, the reaction container which is stirred by the stirring member and is gripped by the chuck portion along the slide rail in order to insert the reaction container back into the installing hole of the installing device;
        collecting by the magnet, the magnetic particles in the stirred reaction container held in the installing hole; and
        removing the washing liquid using the suction nozzle while the magnet collects the magnetic particles.

2. The device according to claim 1, wherein the magnet is positioned on a side of the reaction container held in the installing hole, the discharging tube removes the residue using the suction nozzle while the magnetic particles are collected on the side of the reaction container by the magnet.

3. The device according to claim 1, wherein the suction nozzle is integrated with the supply port and the supply port is configured to supply the washing liquid from above the suction port of the suction nozzle in the reaction container.

4. The device according to claim 1, wherein the stirring mechanism device moves the chuck portion gripping the reaction container along the slide rail between the stir position and an installing position at which the reaction container is held in the installing hole.

5. The device according to claim 1, wherein the motor and the eccentric weight generate vibration to stir the magnetic particles and the washing liquid in the reaction container which is gripped by the chuck portion.

6. The device according to claim 1, wherein the controller is further configured to perform:
    re-resupplying by the supplying device, a washing liquid stored in the tank to the reaction container from which has been removed the washing liquid,
    re-raising the reaction container to the stir position by the stirring mechanism,
    re-stirring the magnetic particles and the re-supplied washing liquid in the reaction container by the stirring mechanism at the stir position;
    re-lowering the reaction container by the stirring mechanism into the installing hole;
    re-collecting the magnetic particles by the magnet, and
    re-removing the re-supplied washing liquid using the suction nozzle while the magnet re-collects the magnetic particles.

7. The device according to claim 1, wherein the analyzer further comprises a nozzle cleaning section having a cleaning hole for inserting the suction nozzle, wherein the supplying device supplies the washing liquid stored in the tank to the cleaning hole in which the suction nozzle is inserted.

8. A separation processing device used in an analyzer for measuring a target substance in a biological sample, comprising:
    an installing device having a plurality of installing holes for holding a respective reaction container containing a reacted sample prepared by reacting a target substance contained in a biological sample and magnetic particles for capturing the target substance;
    a corresponding magnet which is embedded within the installing device in close proximity adjacent to a side of each of the installing hole;
    a discharging tube including a suction nozzle which has a suction port at a lower end;
    a supplying device including a supply port having a tube connecting the supply port to a tank which stores a washing liquid;

a stirring mechanism device including:
  a slide rail extending in a vertical z direction,
  a movement member which moves in the vertical z direction along the slide rail, and
  a stirring member including a pair plate members configured to grip the reaction container, a supporting member attached to the movement member and configured to support the pair of plate members, a motor attached to the supporting member and an eccentric weight driven by the motor; and
a controller configured to control the separation processing device, wherein the controller configures the separation processing device to perform steps in sequence, comprising:
prior to stirring the reaction container, collecting magnetic particles in the reaction container held in the installing hole by the magnet;
removing a residue other than the magnetic particles by the discharging tube while the magnet collects the magnetic particles which are left behind in the reaction container;
supplying by the supplying device, the washing liquid into the reaction container from which the residue has been removed;
raising by the movement member, the reaction container which contains the washing liquid and is gripped by the pair plate members along the slide rail to a stir position which is positioned above the installing hole of the installing device;
stirring the left behind magnetic particles and the washing liquid in the reaction container at the stir position by the stirring member,
lowering by the movement member, the reaction container stirred by the stirring member from the stir position into the installing hole of the installing device;
collecting the magnetic particles in the stirred reaction container held in the installing hole by the magnet; and
removing the washing liquid using the suction nozzle while the magnet collects the magnetic particles.

9. The device according to claim 8, wherein an upper part of the reaction container held in the installing hole is out of the installing hole, and the pair plate members grips the upper part of the reaction container.

10. The device according to claim 8, wherein the suction nozzle is configured to suction the residue from a suction port at the lower end.

11. The device according to claim 10, wherein the suction nozzle is integrated with the supply port and the supply port is configured to supply the washing liquid from above the suction port of the suction nozzle in the reaction container.

12. The device according to claim 1, wherein the analyzer further comprises:
a first reaction processing device configured to prepare the reacted sample by reacting the target substance and the magnetic particles in the reaction container, the first reaction processing device comprising a specimen dispensing arm for dispensing the biological sample in the reaction container and a first reagent dispensing arm for dispensing a first reagent containing the magnetic particles in the reaction container;
a second reaction processing device configured to prepare a second reacted sample by reacting the target substance captured by the magnetic particles and a labeled substance for binding the target substance in the reaction container, the second reaction processing device comprising a second reagent dispensing arm for dispensing a second reagent containing the labeled substance in the reaction container; and
a detecting device including a photo-multiplier tube and configured to measure the target substance by detecting the labeled substance bound to the target substance using the photo-multiplier tube, wherein the separation processing device is configured to separate the magnetic particles from the reacted sample.

13. The device according to claim 12, wherein the analyzer further comprises a second separation processing device configured to separate the magnetic particles from the second reacted sample, comprising:
a second installing device having a second installing hole for holding the reaction container containing the second reacted sample;
a second magnet configured to collect the magnetic particles in the reaction container held in the second installing hole;
a second discharging tube including a second suction nozzle which has a second suction port at the lower end;
a second supplying device including a second supply port having a second tube connecting the second supply port to the tank; and
a second stirring mechanism device including a second slide rail extending in the vertical direction, a second movement member configured to move in the vertical direction along the second slide rail and a second stirring member which is attached to the second movement member and includes a second chuck portion configured to grip the reaction container, a second motor and a second eccentric weight attached to a shaft of the motor;
wherein the controller is configured to control the second separation processing device to perform steps comprising:
prior to stirring the reaction container, collecting magnetic particles in the reaction container held in the second installing hole by the second magnet;
removing a residue other than the magnetic particles by the second discharging tube while the second magnet collects the magnetc particles which are left behind in the reaction container;
supplying by the second supplying device, the washing liquid into the reaction container from which the residue has been removed;
raising by the second movement member, the reaction container which contains the washing liquid and is gripped by the second chuck portion along the second slide rail to a second stir position which is out of the second installing hole and is positioned above the second installing hole;
stirring the left behind magnetic particles and the washing liquid in the reaction container which is gripped by the second chuck portion at the second stir position using the second motor and the second eccentric weight;
lowering by the second movement member, the reaction container stirred by the second stirring member along the second slide rail so as to insert the reaction container in the second installing hole;
collecting by the second magnet, the magnetic particles in the reaction container held in the second installing hole; and
remove removing the washing liquid using the second suction nozzle while the second magnet collects the magnetic particles.

14. The device according to claim 8, wherein the analyzer comprises:
   a first reaction processing device configured to prepare the reacted sample by reacting the target substance and the magnetic particles in the reaction container, the first reaction processing device comprising a specimen dispensing arm for dispensing the biological sample in the reaction container and a first reagent dispensing arm for dispensing a first reagent containing the magnetic particles in the reaction container;
   a second reaction processing device configured to prepare a second reacted sample by reacting the target substance captured by the magnetic particles and a labeled substance for binding the target substance in the reaction container, the second reaction processing device comprising a second reagent dispensing arm for dispensing a second reagent containing the labeled substance in the reaction container; and
   a detecting device including a photo-multiplier tube and configured to measure the target substance by detecting the labeled substance bound to the target substance using the photo-multiplier tube,
   wherein the separation processing device is configured to separate the magnetic particles from the second reacted sample.

15. An analyzing apparatus for measuring a target substance in a biological sample, comprising:
   a first reaction processing device configured to prepare a first reacted sample by reacting a target substance in a biological sample and magnetic particles for capturing the target substance in a reaction container, the first reaction processing device comprising a specimen dispensing arm for dispensing the biological sample in the reaction container and a first reagent dispensing arm for dispensing a first reagent containing the magnetic particles in the reaction container;
   a second reaction processing device configured to prepare a second reacted sample by reacting the target substance captured by the magnetic particles and a labeled substance for binding the target substance in the reaction container, the second reaction processing device comprising a second reagent dispensing arm for dispensing a second reagent containing the labeled substance in the reaction container;
   a separation processing device configured to separate the magnetic particles from the first reacted sample or the second reacted sample;
   a detecting device including a photo-multiplier tube and configured to measure the target substance by detecting the labeled substance bound to the target substance using the photo-multiplier tube; and
   a controller configured to control the analyzing apparatus, wherein the separation processing device comprises:
   an installing device having a plurality of installing holes for holding a respective reaction container containing the first reacted sample or the second reacted sample;
   a corresponding magnet which is embedded within the installing device in close proximity adjacent to a side of each of the installing hole;
   a discharging tube including a suction nozzle which has a suction port at a lower end;
   a supplying device including a supply port having a tube connecting the supply port to a tank which stores a washing liquid;
   a slide rail extending in the vertical z direction;
   a movement member configured to move in the vertical z direction along the slide rail; and
   a stirring member including a pair plate members which is configured to grip the reaction container, a supporting member attached to the movement member and is configured to support the pair of plate members, a motor attached to the supporting member and an eccentric weight driven by the motor,
   wherein the controller is configured to perform steps in sequence, comprising:
      prior to stirring the reaction container, collecting magnetic particles in the reaction container held in the installing hole by the magnet;
      removing a residue other than the magnetic particles by the discharging tube while the magnet collects the magnetic particles which are left behind in the reaction container;
      supplying by the supplying device, the washing liquid into the reaction container from which the residue has been removed;
      raising by the movement member, the reaction container which contains the washing liquid and is gripped by the pair plate members along the slide rail at a stir position above the installing hole;
      stirring by the stirring member, the let behind magnetic particles and the washing liquid in the reaction container;
      lowering by the movement member, the reaction container stirred by the stirring member from the stir position into the installing hole;
      collecting by the magnet, the magnetic particles in the stirred reaction container held in the installing hole of the installing device; and
      removing the washing liquid using the suction nozzle while the magnet collects the magnetic particles.

16. The analyzing apparatus according to claim 15, wherein the suction nozzle has a suction port at the lower end, the suction nozzle is integrated with the supply port, and the supply port is configured to supply the washing liquid stored in the tank from above the suction port of the suction nozzle in the reaction container.

17. An analyzing apparatus for measuring a target substance in a biological sample, comprising:
   a first reaction processing device configured to prepare a first reacted sample by reacting a target substance in a biological sample and magnetic particles for capturing the target substance in a reaction container the first reaction processing device comprising a specimen dispensing arm for dispensing the biological sample in the reaction container and a first reagent dispensing arm for dispensing a first reagent containing the magnetic particles in the reaction container;
   a first separation processing device configured to separate the magnetic particles from the first reacted sample;
   a second reaction processing device configured to prepare a second reacted sample by reacting the target substance captured by the magnetic particles and a labeled substance for binding the target substance in the reaction container, the second reaction processing device comprising a second reagent dispensing arm for dispensing a second reagent containing the labeled substance in the reaction container;
   a second separation processing device configured to separate the magnetic particles from the second reacted sample;
   a detecting unit including a photo-multiplier tube and configured to measure the target substance by detecting the labeled substance bound to the target substance using the photo-multiplier tube; and a controller configured to control the analyzing apparatus, wherein the first separation processing device comprises:
an installing device having a plurality of installing holes for holding a respective reaction container containing the first reacted sample;
a corresponding magnet which is embedded within the installing device in close proximity adjacent to a side of each of the installing hole;
a discharging tube including a suction nozzle which has a suction port at a lower end;
a supplying device including a supply port having a tube connecting the supply port to a tank which stores a washing liquid;
a slide rail extending in the vertical direction;
a movement member configured to move in the vertical direction along the slide rail; and
a stirring member including a pair plate members which are configured to grip the reaction container, a supporting member attached to the movement member and configured to support the pair of plate members, a motor attached to the supporting member and an eccentric weight driven by the motor,
wherein the controller is configured to perform steps in sequence, comprising:
prior to stirring the reaction container, collecting magnetic particles in the reaction container held in the installing hole by the magnet;
removing a residue other than the magnetic particles by the discharging tube while the magnet collects the magnetic particles which are left behind in the reaction container;
supplying by the supplying device, the washing liquid into the reaction container from which the residue has been removed;
raising by the movement member, the reaction container contains the washing liquid and is gripped by the pair plate members along the slide rail at a stir position which is out of the installing hole and is positioned above the installing hole of the installing device;
stirring the left behind magnetic particles and the washing liquid in the reaction container at the stir position by the stirring member;
lowering by the movement member, the reaction container stirred by the stirring member from the stir position into the installing hole;
collecting the magnetic particles in the stirred reaction container held in the installing hole by the magnet; and
removing the washing liquid using the suction nozzle while the magnet collects the magnetic particles.

18. The analyzing apparatus according to claim 17, wherein the second separation processing device comprises:
a second installing device having a plurality of installing holes for holding the respective reaction container contaiing the second reacted sample;
a corresponding second magnet which is embedded within the second installing device in close proximity adjacent to a side of each of the installing hole;
a second discharging tube including a second suction nozzle:
a second supplying device including a second supply port and second tube connected to the second supply port and the tank;
a second slide rail extending in the vertical direction;
a second movement member configured to move in the vertical direction along the second slide rail; and
a second stirring member including a second pair plate members are configured to grip the reaction container, a second supporting member attached to the second movement member and configured to support the second pair of plate members, a second motor attached to the second supporting member and a second eccentric weight driven by the second motor,
wherein the controller is configured to perform steps comprising:
collecting magnetic particles in the reaction container held in the second installing hole by the second magnet;
removing a residue other than the magnetic particles by the second discharging tube while the second magnet collects the magnetic particles which are left behind in the reaction container;
supplying by the second supplying device, the washing liquid into the reaction container from which the residue has been removed;
raising by the second movement member, the reaction container which is gripped by the second pair plate members along the second slide rail to a second stir position above the second installing hole,
stirring the magnetic particles and the washing liquid in the reaction container at the second stir position by vibration of the second eccentric weight driven by the second motor,
lowering by the second movement member, the reaction container stirred by the second stirring member from the second stir position into the second installing hole,
collecting by the second magnet, the magnetic particles in the stirred reaction container held in the second installing hole, and
removing the washing liquid using the second suction nozzle while the second magnet collects the magnetic particles.

* * * * *

UNITED STATES PATENT AND TRADEMARK OFFICE
CERTIFICATE OF CORRECTION

| | |
|---|---|
| PATENT NO. | : 9,594,089 B2 |
| APPLICATION NO. | : 14/662741 |
| DATED | : March 14, 2017 |
| INVENTOR(S) | : Toshihiro Ootani et al. |

It is certified that error appears in the above-identified patent and that said Letters Patent is hereby corrected as shown below:

In the Claims

In Column 34, Claim 13, Line 43, after "collects the" replace "magnetc" with --magnetic--.

In Column 34, Claim 13, Line 65, before "removing the washing" delete "remove".

In Column 36, Claim 15, Line 23, after "member, the" replace "let" with --left--.

In Column 38, Claim 18, Line 5, before "the second reacted" replace "contaiing" with --containing--.

Signed and Sealed this
Eighth Day of August, 2017

Joseph Matal
*Performing the Functions and Duties of the*
*Under Secretary of Commerce for Intellectual Property and*
*Director of the United States Patent and Trademark Office*